(12) United States Patent
Hayashida

(10) Patent No.: US 9,851,789 B2
(45) Date of Patent: Dec. 26, 2017

(54) INFORMATION PROCESSING TECHNIQUE FOR EYE GAZE MOVEMENTS

(71) Applicant: FUJITSU LIMITED, Kawasaki-shi, Kanagawa (JP)

(72) Inventor: Naoko Hayashida, Yokohama (JP)

(73) Assignee: FUJITSU LIMITED, Kawasaki (JP)

(*) Notice: Subject to any disclaimer, the term of this patent is extended or adjusted under 35 U.S.C. 154(b) by 209 days.

(21) Appl. No.: 14/616,886

(22) Filed: Feb. 9, 2015

(65) Prior Publication Data

US 2015/0277556 A1 Oct. 1, 2015

(30) Foreign Application Priority Data

Mar. 31, 2014 (JP) .................................. 2014-071251

(51) Int. Cl.
  *G06K 9/00* (2006.01)
  *G06F 3/01* (2006.01)
  *A61B 3/113* (2006.01)

(52) U.S. Cl.
  CPC ........... *G06F 3/013* (2013.01); *G06K 9/0061* (2013.01); *G06K 9/00604* (2013.01); *A61B 3/113* (2013.01)

(58) Field of Classification Search
  USPC .......... 128/898; 345/156, 173, 661; 351/209
  See application file for complete search history.

(56) References Cited

U.S. PATENT DOCUMENTS

| | | | | |
|---|---|---|---|---|
| 4,889,422 A * | 12/1989 | Pavlidis | ............... | A61B 3/113 128/898 |
| 6,152,563 A * | 11/2000 | Hutchinson | ............ | A61B 3/113 351/209 |
| 6,608,615 B1 * | 8/2003 | Martins | .................... | G06F 3/013 345/156 |
| 8,719,278 B2 * | 5/2014 | Karmarkar | ........ | G06F 17/30032 707/748 |
| 8,767,014 B2 * | 7/2014 | Vaught | .................. | G02B 27/017 345/633 |
| 9,198,571 B2 * | 12/2015 | Kiderman | ............... | A61B 3/145 |
| 9,642,522 B2 * | 5/2017 | Samadani | ............... | A61B 3/113 |
| 2004/0252277 A1 | 12/2004 | Chmielewski, Jr. et al. | | |
| 2010/0039618 A1 | 2/2010 | De Lemos | | |

(Continued)

FOREIGN PATENT DOCUMENTS

| | | |
|---|---|---|
| CA | 1304788 | 7/1992 |
| JP | 05-056925 | 3/1993 |

(Continued)

OTHER PUBLICATIONS

Asteriadis; "Estimation of Behavioral User State Based on Eye Gaze and Head Pose—Application in an E-Learning Environment" Multimedia Tools Appl, vol. 41, Issue 3, pp. 469-493, 2009.

(Continued)

*Primary Examiner* — Xuemei Chen
(74) *Attorney, Agent, or Firm* — Staas & Halsey LLP

(57) ABSTRACT

An information processing method relating to movement of eye positions includes: identifying, for each of plural users, transition of movement directions of an eye gaze of the user, from movement history of the eye gaze of the user on a display screen; and extracting a minor user among the plural users based on the transition of the movement directions of the eye gaze, which is identified for each of the plural users.

5 Claims, 27 Drawing Sheets

(56) References Cited

U.S. PATENT DOCUMENTS

| | | | |
|---|---|---|---|
| 2012/0105486 A1* | 5/2012 | Lankford | G06F 3/013 345/661 |
| 2012/0131491 A1 | 5/2012 | Lee | |
| 2012/0323796 A1 | 12/2012 | Udani | |
| 2013/0021458 A1 | 1/2013 | Inoue et al. | |
| 2013/0027302 A1 | 1/2013 | Iwaizumi et al. | |
| 2013/0131521 A1 | 5/2013 | Yoshioka et al. | |
| 2014/0015778 A1* | 1/2014 | Taguchi | G06F 3/041 345/173 |
| 2014/0148728 A1* | 5/2014 | Eizenman | A61B 5/1104 600/558 |
| 2015/0213634 A1* | 7/2015 | Karmarkar | G06T 11/60 345/589 |
| 2016/0029883 A1* | 2/2016 | Cox | G06F 3/013 351/209 |
| 2016/0095511 A1* | 4/2016 | Taguchi | A61B 3/0025 351/209 |

FOREIGN PATENT DOCUMENTS

| | | |
|---|---|---|
| JP | 2002-149332 | 5/2002 |
| JP | 2013-025656 | 2/2013 |
| WO | WO 2012/150657 A1 | 11/2012 |

OTHER PUBLICATIONS

Chandan Singh et al: "User Ranking by Monitoring Eye Gaze Using Eye Tracker" In: "Biologically Inspired Cognitive Architectures 2012", Mar. 4, 2014, vol. 258, pp. 235-246.

Terje Falck-Ytter et al: "Eye tracking in early autism research", Journal of Neurodevelopmental Disorders, Biomed Central LTD, vol. 5, No. 1, Sep. 26, 2013, p. 28.

European Extended Search Report dated Jul. 3, 2015 in corresponding European Application No. 15153718.0.

European Office Action dated Nov. 16, 2016 in corresponding European Patent Application No. 15 153 718.0.

* cited by examiner

FIG.8

| TIME | USER | SCREEN | WINDOW ID | X COORDINATE OF UPPER LEFT | Y COORDINATE OF UPPER LEFT | WIDTH | HEIGHT | TURN IN DEPTH DIRECTION OF SCREEN |
|---|---|---|---|---|---|---|---|---|
| 2012/7/12 11:00:01.030 | userR1 | scrB | 1 | 10 | 10 | 300 | 300 | 1 |
| 2012/7/12 11:00:01.030 | userR1 | scrB | 2 | 100 | 10 | 500 | 500 | 2 |
| 2012/7/12 11:00:01.069 | userR1 | scrB | 1 | 10 | 10 | 300 | 1000 | 1 |
| ... | ... | ... | ... | ... | ... | ... | ... | ... |

FIG.9

| TIME | USER | SCREEN | WINDOW ID | CONTENTS ID | TIME SECTION OF CONTENTS |
|---|---|---|---|---|---|
| 2012/7/12 11:00:01.030 | userR1 | scrB | 1 | 1 | 1 |
| 2012/7/12 11:00:01.030 | userR1 | scrB | 2 | 2 | 100 |
| 2012/7/12 11:00:01.069 | userR1 | scrB | 1 | 1 | 2 |
| ... | ... | ... | ... | ... | ... |

FIG.11

| TIME | USER | SCREEN | X COORDINATE | Y COORDINATE | COORDINATE TYPE |
|---|---|---|---|---|---|
| 2012/7/12 11:00:01.030 | userR1 | scrB | 10 | 10 | ABSOLUTE COORDINATES ON SCREEN |
| 2012/7/12 11:00:01.030 | userR1 | scrB | 100 | 10 | ABSOLUTE COORDINATES ON SCREEN |
| 2012/7/12 11:00:01.069 | userR1 | scrB | 10 | 10 | ABSOLUTE COORDINATES ON SCREEN |
| ... | ... | ... | ... | ... | ... |

FIG.12

| TIME | USER | SCREEN | X COORDINATE | Y COORDINATE | COORDINATE TYPE |
|---|---|---|---|---|---|
| 2012/7/12 11:00:01.030 | userR1 | scrB | 10 | 0 | COORDINATE VALUES ON WINDOW |
| 2012/7/12 11:00:01.030 | userR1 | scrB | 90 | 0 | COORDINATE VALUES ON WINDOW |
| 2012/7/12 11:00:01.069 | userR1 | scrB | 0 | 0 | COORDINATE VALUES ON WINDOW |
| ... | ... | ... | ... | ... | ... |

| TIME t | 1 | 2 | 3 | 4 | 5 | 6 | 7 |
|---|---|---|---|---|---|---|---|
| X AXIS | 200 | 10 | 80 | 450 | 200 | −10 | − |
| Y AXIS | −200 | −200 | −80 | 450 | 10 | −290 | − |

FIG.20

| TIME t | 1 | 2 | 3 | 4 | 5 | 6 | 7 |
|---|---|---|---|---|---|---|---|
| X AXIS | R | − | R | R | R | − | − |
| Y AXIS | D | D | D | U | − | D | − |

FIG.21

| TIME t | 0−2 | 2−4 | 4−6 | 6−8 | 8−10 | 10−12 | 12−14 |
|---|---|---|---|---|---|---|---|
| X AXIS | R | − | R | − | R | R | − |
| Y AXIS | D | D | − | U | − | D | D |

FIG.22

|  | USER | 0-2 | 2-4 | 4-6 | 6-8 | 8-10 | 10-12 | 12-14 |
|---|---|---|---|---|---|---|---|---|
| X AXIS | userR1 | R | – | R | – | R | R | – |
|  | userR2 | R | R | – | R | R | R | R |
|  | ⋮ | ⋮ | ⋮ | ⋮ | ⋮ | ⋮ | ⋮ | ⋮ |
|  | userRn | L | – | R | – | R | R | – |
|  | MAJORITY | R | – | R | R | R | R | – |
| Y AXIS | userR1 | D | D | – | U | – | D | D |
|  | userR2 | – | D | D | D | U | U | D |
|  | ⋮ | ⋮ | ⋮ | ⋮ | ⋮ | ⋮ | ⋮ | ⋮ |
|  | userRn | U | D | U | D | U | U | D |
|  | MAJORITY | – | D | – | D | U | U | D |

FIG.24

| TIME t | 0-2 | 2-4 | 4-6 | 6-8 | 8-10 | 10-12 | 12-14 |
|---|---|---|---|---|---|---|---|
| SIMILARITY FOR X AXIS | 1 | 0.5 | 1 | 0.5 | 1 | 1 | 0.5 |
| SIMILARITY FOR Y AXIS | 0.5 | 1 | 0.5 | 0 | 0.5 | 0 | 1 |

FIG.25

|  | TIME USER | 0-2 | 2-4 | 4-6 | 6-8 | 8-10 | 10-12 | 12-14 |
|---|---|---|---|---|---|---|---|---|
| RECTANGULAR AREA | userR1 | 10000 | 100 | 100 | 200 | 400 | 40000 | 100 |
| | userR2 | 900 | 400 | 100 | 400 | 900 | 10000 | 900 |
| | ... | ... | ... | ... | ... | ... | ... | ... |
| | userRn | 100 | 100 | 10000 | 100 | 400 | 40000 | 100 |
| CENTRAL POINT OF RECTANGLE | userR1 | (150, 200) | (200, 300) | (250, 320) | (220, 300) | (400, 310) | (500, 400) | (510, 410) |
| | userR2 | (200, 300) | (210, 310) | (220, 320) | (230, 300) | (240, 290) | (540, 590) | (550, 600) |
| | ... | ... | ... | ... | ... | ... | ... | ... |
| | userRn | (40, 50) | (50, 70) | (200, 170) | (210, 180) | (240, 170) | (350, 150) | (360, 200) |

FIG.30

|        | userR1 | userR2 | ... | userRn | SIMILARITY WITH ALL OTHER USERS |
|--------|--------|--------|-----|--------|--------------------------------|
| userR1 |        | 0.09/0.94 | ... | 0.01/0.91 | 0.06/0.92 |
| userR2 | ...    |        | ... | 0.11/0.85 | 0.21/0.88 |
| ⋮      | ⋮      | ⋮      |     | ⋮      | ⋮ |
| userRn | ...    | ...    | ... |        | 0.03/0.90 |

| TIME t | 1 | 2 | 3 | 4 | 5 | 6 | 7 |
|--------|---|---|---|---|---|---|---|
| X AXIS | 200 | – | 80 | 300 | 200 | – | – |
| Y AXIS | –200 | –200 | –80 | 300 | – | –290 | – |

INFORMATION PROCESSING TECHNIQUE FOR EYE GAZE MOVEMENTS

CROSS-REFERENCE TO RELATED APPLICATIONS

This application is based upon and claims the benefit of priority of the prior Japanese Patent Application No. 2014-071251, filed on Mar. 31, 2014, the entire contents of which are incorporated herein by reference.

FIELD

This invention relates to an information processing technique based on movement of eye positions on a display screen.

BACKGROUND

When an eye tracker (this is provided, for example, above or below a display screen) is a high-end model, it is possible to presume that a user in front of the display screen reads displayed sentences along them or gives a sentence area a once-over based on measured eye gaze data (i.e. data of the line of sight).

On the other hand, when a low-end eye tracker is used, an error included in the measured eye gaze data tends to become larger than that of the high-end model. For example, even when one eye position on a typical display screen of a personal computer is detected, a true eye position is located inside of an area that includes the one eye position and is about ⅙ of the display screen.

In such a case, even when the user reads a document along the sentences, it is not expected that coordinates of the eye position obtained from the measured eye gaze data are included in the sentence area. Moreover, it is difficult to accurately determine, according to the arrangement of the measured eye gaze data in time series, whether or not transition of eye gaze directions of a certain user is identical with transition of eye gaze directions of another user.

For example, if partial missing of a task to check a document or skip of reading of important portions is detected in a case where people check contents in the same document (for example, checking whether all required fields in a document are filled in or not, or whether all important points are read in a online educational document or not), it is possible to output an alarm to corresponding users. However, the low-end eye tracker cannot detect the aforementioned reading activities with high accuracy.

There is a technique to determine, based on the eye position data and transition speed of the eye position, whether an electronic document displayed on a display unit has been read or not. However, because the technique to determine whether a person read or not depends on the eye position, it is presupposed that the accuracy of the eye tracker is high.

Moreover, although there is a technique that presupposes that the eye tracker is the low-end model, it is determined based on the transition speed of the eye position and curvature obtained from temporal change of the eye positions, whether the user watches a certain area with his or her attention or not. In such a technique, there is no consideration to estimate the relationship between reading activity tendency the user of and that of other users.

Patent Document 1: Japanese Laid-open Patent Publication No. 2013-25656

Patent Document 2: Japanese Laid-open Patent Publication No. 05-56925

In other words, in conventional arts, there is no technique to enable to detect a user that does not perform typical movement of the eye gaze on a display screen, even when the eye tracker having low accuracy is used.

SUMMARY

An information processing method relating to this invention includes: (A) identifying, for each of plural users, transition of movement directions of an eye of the user, from movement history of the eye gaze of the user on a display screen; and (B) extracting a minor user among the plural users based on the transition of the movement directions of the eye gaze, which is identified for each of the plural users.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 8 is a diagram depicting an example of data stored in a collected data storage unit;

FIG. 9 is a diagram depicting an example of data stored in the collected data storage unit;

FIG. 11 is a diagram depicting an example of data stored in the collected data storage unit;

FIG. 12 is a diagram depicting an example of data stored in the collected data storage unit;

FIG. 20 is a diagram depicting an example of a calculated substantial movement amount;

FIG. 21 is a diagram depicting an example of labeling of the movement direction;

FIG. 22 is a diagram depicting an example of aggregating the labels of the movement directions;

FIG. 24 is a diagram to explain a processing for determining the majority from the labels of the movement directions for plural users;

FIG. 25 is a diagram depicting an example of calculating a similarity in the first embodiment;

FIG. 30 is a diagram depicting an example of processing results of a rectangle processing unit;

DESCRIPTION OF EMBODIMENTS

Embodiment 1

In this embodiment, transition of movement directions of the eye gaze is identified for each user. And a user is detected, whose transition of the movement directions of the eye gaze is different from the typical transition of the movement directions of the eye gaze. There is a possibility that such a user partially forgot the document check in a task to check whether all required fields in a document are filled in or skipped reading of important parts in online education or the like. Therefore, by outputting an alarm to such a user or an administrator, it is possible to prevent the partial omission of the document check or the skip of the reading of the important parts in online education.

However, as described above, when a low-end eye tracker is used, the measured eye position includes an error, and it is not preferable that the transition of the movement directions of the eye gaze is simply identified based on the measured eye positions. On the other hand, even when the low-end eye tracker is used, it is possible to identify a situation that the line of sight is moved as illustrated in (b) of FIG. 1 from a state where the user gazed steadily in the vicinity of an area A in the display screen as illustrated in (a) of FIG. 1, and the state is changed to a state that the user gazes steadily in the vicinity of an area B as illustrated in (c) of FIG. 1.

Figure 1:
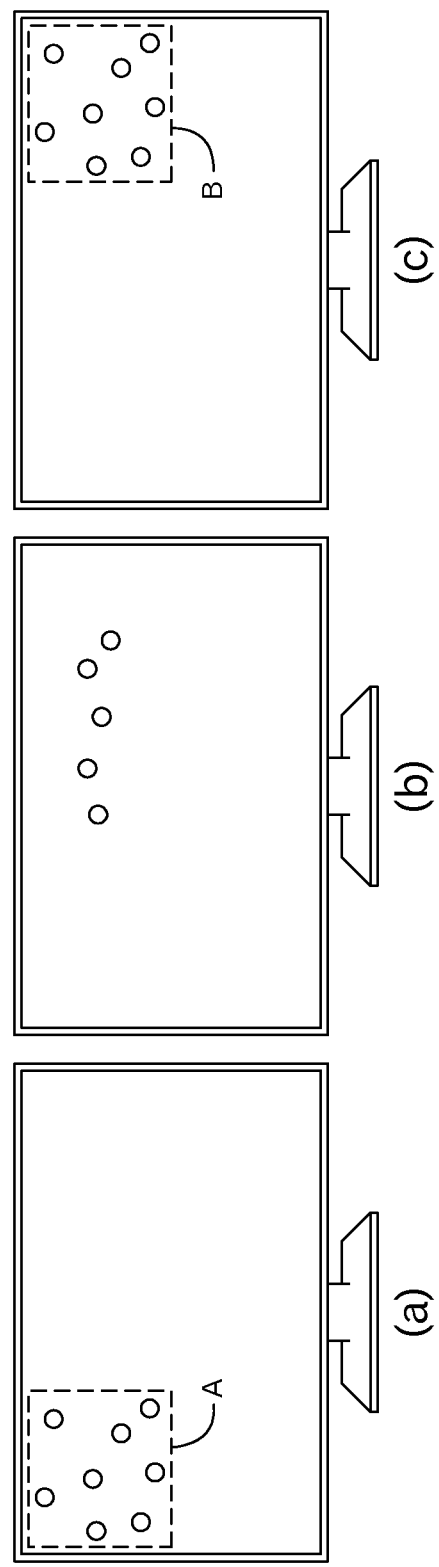
FIG. 1 is a diagram to explain detection results of the eye gaze by using an eye tracker having low accuracy.

In this embodiment, even in states of the steady gazes as illustrated in (a) and (c) of FIG. 1, trends of movement directions of the eye gaze can be extracted, and data representing the transition of the movement directions of the eye gaze is generated based on the trends of the movement directions of the eye gaze.

Figure 2:
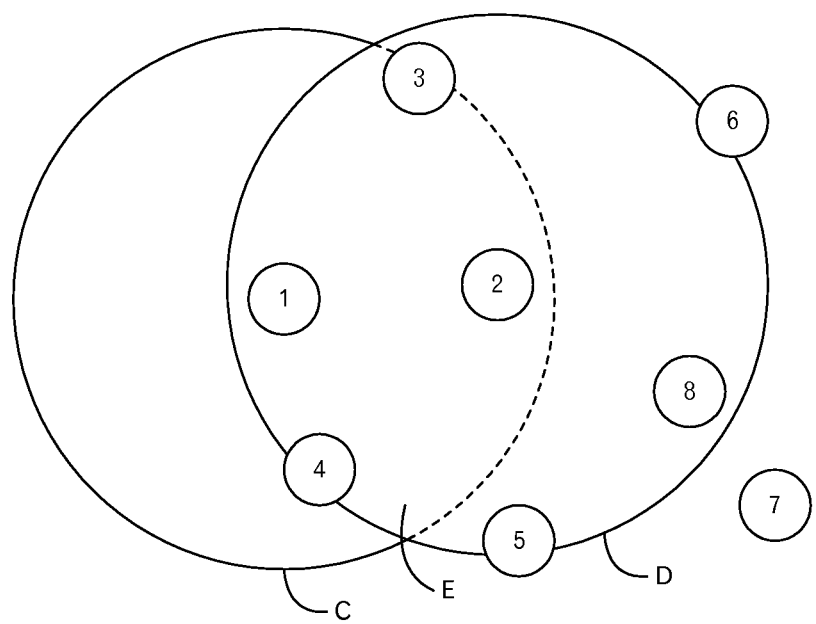
FIG. 2 is a diagram to explain trends of eye movements.

More specifically, as illustrated in FIG. 2, a state is assumed that 8 eye positions are detected, for example. Here, a first eye position and a second eye position are focused on. Then, when considering an error, the first eye position exists in a range of circle C, and when considering an error, the second eye position exists in a range of circle D, and when the eye position is moved from the first eye position to the second eye position, there is a possibility that the eye position moves to an area E in which the circle C overlaps with the circle D. This area E represents the trend of the movement directions, for which the error is considered into account, however, it is difficult to handle the area E as it is. Therefore, in this embodiment, the trend of the movement directions of the eye gaze is expressed by a method that will be explained later.

In other words, the substantial movement direction of the eye gaze is calculated based on not only an eye position to be focused on and a next eye position but also further subsequent eye positions. More specifically, a substantial movement amount is calculated by accumulating, for each direction of X-axis and Y-axis on the display screen, movement amounts from the eye position to be focused on until the reverse of the movement direction is detected within a predetermined duration of time.

Figure 3:
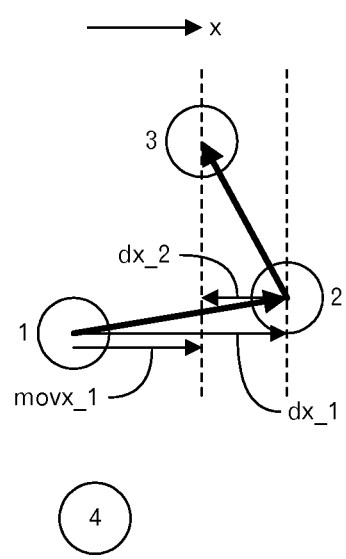
FIG. 3 is a diagram to explain a substantial movement amount of the eye gaze.

The first eye position in FIG. 2 is focused on, and it is determined whether or not a return of the eye gaze exists within a duration of time up to the n-th eye positions (n is a positive integer. For example, n=6). As for the X-axis direction, as illustrated in FIG. 3, the movement amount from the first eye position to the second eye position is $dx\_1$, and the movement amount from the second eye position to the third eye position is $dx\_2$. However, in the movement from the second eye position to the third eye position, the return of the eye gaze occurred. Then, the substantial movement amount $movx\_1$ from the first eye position in the X-axis direction is represented by "$dx\_1+dx\_2$".

Figure 4:
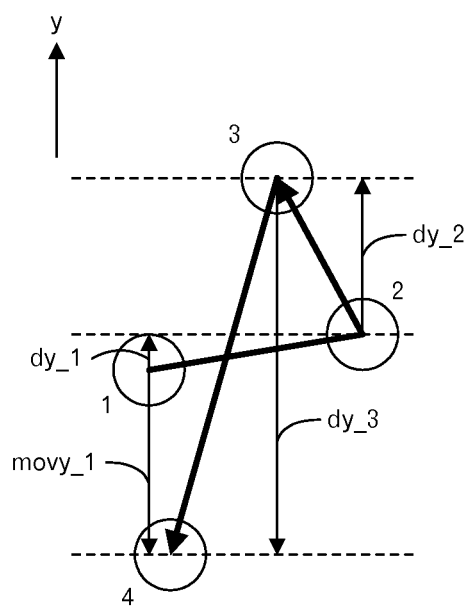
FIG. 4 is a diagram to explain the substantial movement amount of the eye gaze.

Similarly, as for the Y-axis direction, as illustrated in FIG. 4, the movement amount from the first eye position to the second eye position is $dy\_1$, the movement amount from the second eye position to the third eye position is $dy\_2$, and the movement amount from the third eye position to the fourth eye position is $dy\_3$. In the movement from the third eye position to the fourth eye position, a return of the eye gaze occurred. Then, the substantial movement amount $movy\_1$ from the first eye position in the Y-axis direction is represented by "$dy\_1+dy\_2+dy\_3$".

By repeating such calculation for each eye position, the trend of the movement directions for each eye position is calculated. Such calculation is based on characteristics that the total sum of the movement amounts from respective eye positions within the predetermined duration of time approaches zero, although the coordinate values of the respective eye positions are not completely identical when a user watches one point on the display screen, because it is impossible to remove minute movements of the eye as the measurement results.

Then, by summarizing the trends of the movement directions for each predetermined time (hereinafter, referred to a time period), the transition of the movement directions of the eye gaze is determined. Then, a user who is minor among plural users is extracted based on the transition of the movement directions of the eye gaze.

Next, an outline of a system in this embodiment will be explained by using FIG. 5.

In the system in this embodiment, a main information processing apparatus 100 that performs a main processing in this embodiment, plural user-side information processing apparatus 300 (in this figure, 300a to 300n) and an administrator terminal 400 are connected via a network 200.

The user-side information processing apparatus 300a includes an information display apparatus 301a and an information collection apparatus 302a. The information display apparatus 301 displays data such as documents on a display device for a user, and manages data for the display history. The data such as documents may be delivered to the main information processing apparatus 100 or the like, and may be saved in the information display apparatus 301a.

Furthermore, the information collection apparatus 302a has an eye tracker, and collects sensor data regarding the eye positions of the user on the display screen, and the like. For example, the information collection apparatus 302a may include a device such as a Web camera, and calculate the eye positions on the display screen from images photographed by the Web camera. As for detection techniques of the eye position, please refer to Stylianos Asteriadis et al., "Estimation of behavioral user state based on eye gaze and head pose-application in an e-learning environment", Multimed Tools Appl, 2009 and the like. A processing to calculate eye position coordinates (in other words, coordinates of eye position) on the display screen from the sensor data may be performed in the main information processing apparatus 100 or may be performed in the information collection apparatus 302a.

Moreover, the information collection apparatus 302a also collects history data of contents displayed on the display screen of the information display apparatus 301a. The data collected in the information collection apparatus 302a is transmitted through the network 200 to the main information processing apparatus 100.

The information display apparatus 301a and the information collection apparatus 302a may be integrated to form the user-side information processing apparatus 300a. The user-side information processing apparatus 300a may be a mobile phone (including a smart phone), a tablet apparatus, a personal computer or the like. Furthermore, other user-side information processing apparatuses 300b to 300n has the same configuration as that of the user-side information processing apparatus 300a.

The user-side information processing apparatus 300 may be prepared for each user or may be shared by plural users.

The administrator terminal 400 is a terminal apparatus that is operated by an administrator of a system, for example, and when data for a user who did not make the typical transition of the movement directions of the eye gaze is notified from the main information processing apparatus 100, that data is displayed on a display device.

Figure 6:
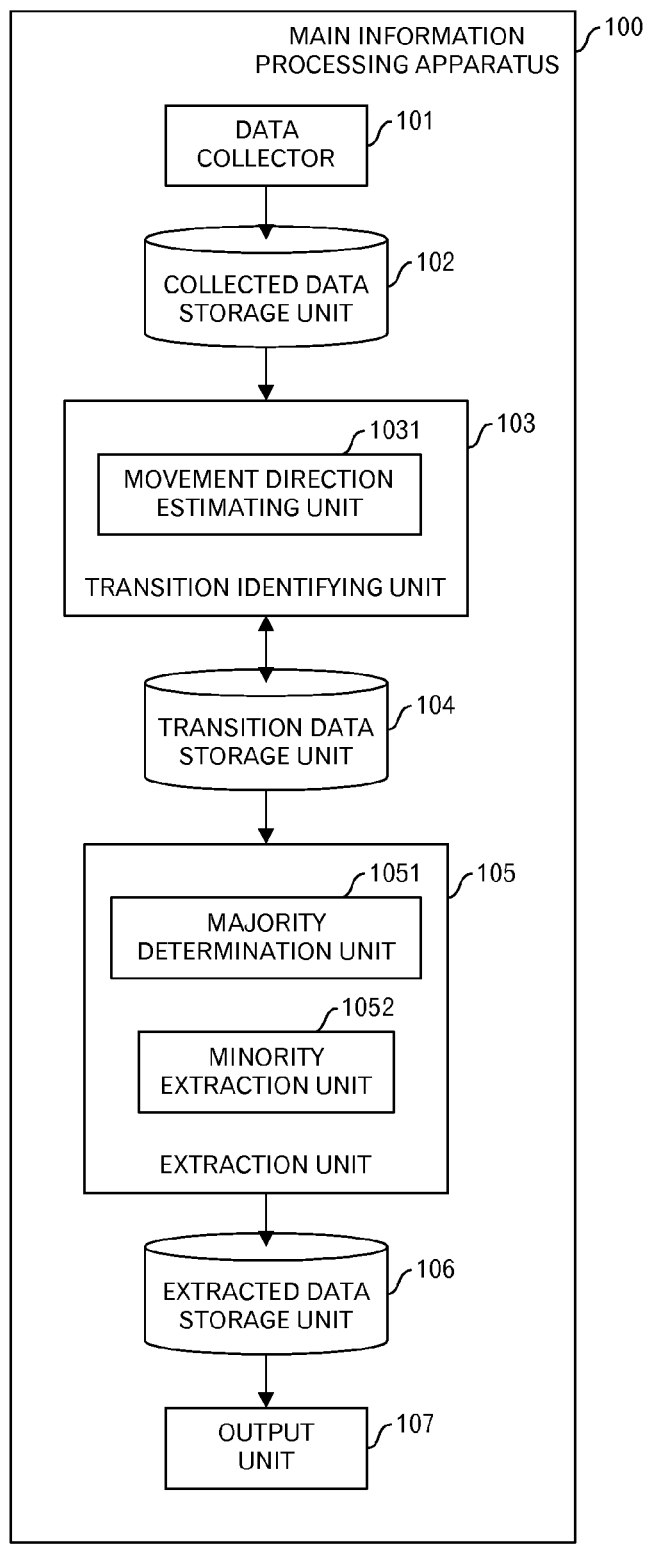
FIG. 6 is a functional block diagram of a main information processing apparatus in a first embodiment.

Next, a configuration example of the main information processing apparatus 100 is illustrated in FIG. 6. The main information processing apparatus 100 has a data collector 101, a collected data storage unit 102, a transition identifying unit 103, a transition data storage unit 104, an extraction unit 105, an extracted data storage unit 106 and an output unit 107.

The data collector 101 receives sensor data and display history data, which are transmitted from the user-side information processing apparatus 300, and stores the received data in the collected data storage unit 102. When the sensor data is not converted into the eye position coordinate data on the display screen, the data collector 101 also performs a data conversion processing (here, conversion means format conversion).

The transition identifying unit 103 has a movement direction estimating unit 1031, and generates data representing the transition of the movement directions of the eye gaze, and stores the generated data in the transition data storage unit 104. The movement direction estimating unit 1031 calculates a substantial movement amount explained by using FIGS. 3 and 4.

The extraction unit 105 has a majority determination unit 1051 and a minority extraction unit 1052, and extracts data for a user who did not make the typical transition of the movement directions of the eye gaze, and stores the extracted data in the extracted data storage unit 106. The majority determination unit 1051 determines the major transition of the movement directions of the eye gaze from the transitions of the movement directions of the eye gaze for plural users. Moreover, the minority extraction unit 1052 extracts a user who made the transition of the movement directions of the eye gaze, which is not similar to the major transition of the movement directions of the eye gaze.

The output unit 107 transmits data for the minor user, which is stored in the extracted data storage unit 106, to the administrator terminal 400, for example. Data may be outputted to other apparatus (including the user-side information processing apparatus 300).

Figure 7:
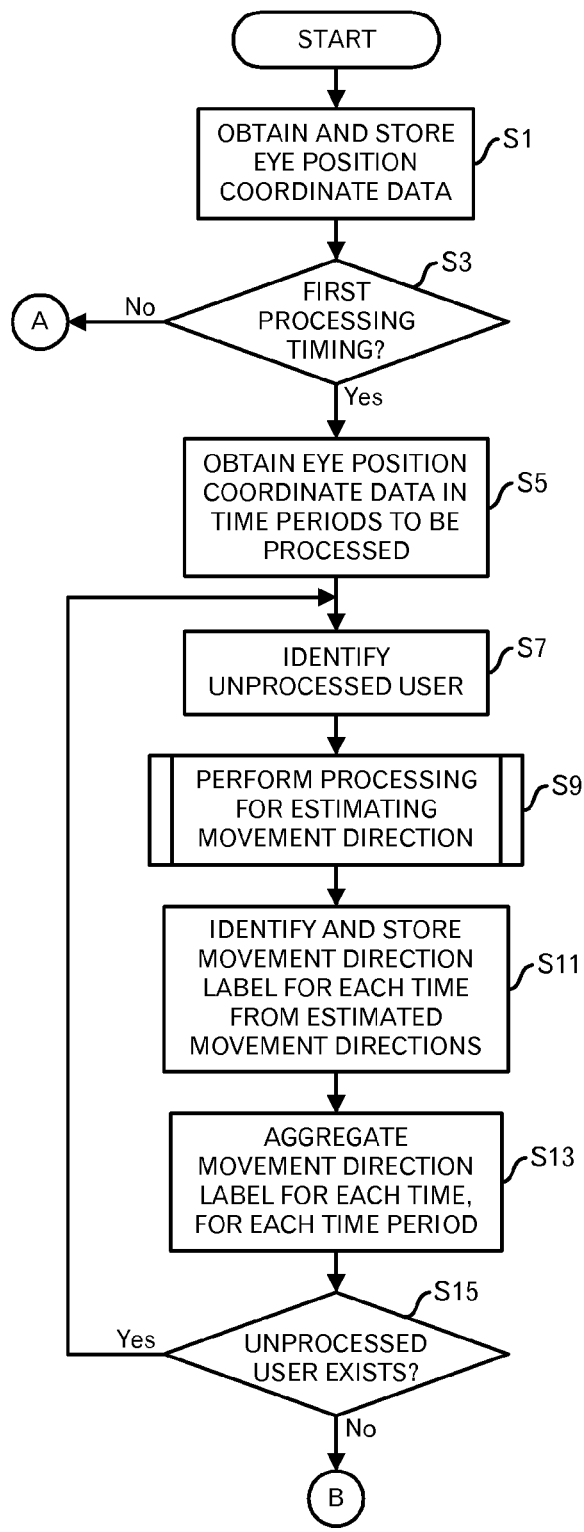
FIG. 7 is a diagram depicting a processing flow in the first embodiment.

Next, a processing in the main information processing apparatus 100 will be explained by using FIGS. 7 to 25. Firstly, the data collector 101 receives the sensor data and display history data from each of the user-side information processing apparatuses 300a to 300n, converts the sensor data into the eye position coordinate data, and stores the converted data in the collected data storage unit 102 (FIG. 7: step S1).

As described above, a document to be checked when a document checking task is performed or an online educational material in the course in case of the online education is displayed on the display screen of the information display apparatus 301, for example. At this time, the information collection apparatus 302 simultaneously obtains sensor data from the eye tracker, further obtains data of the contents being displayed, and transmits the obtained data to the main information processing apparatus 100 in correlation with them each other.

The data collector 101 of the main information processing apparatus 100 receives the sensor data from the eye tracker and the data of the contents from the respective user-side information processing apparatus 300, and stores the received data in the collected data storage unit 102.

FIGS. 8 to 12 illustrate examples of the data of the contents, which are stored in the collected data storage unit 102. Firstly, FIG. 8 illustrates an example of the history data of window coordinates (in other words, x-y coordinates of a window). In the example of FIG. 8, a display time, a user ID (identifier), a screen ID, a window ID, x and y coordinates of the upper left of that window, a width and height of that window and a turn of that window in the depth direction of the screen (in other words, a turn of that window in overlapping windows) are included. Thus, it is possible to grasp what window is displayed on the display screen and which window is a foreground.

Furthermore, FIG. 9 illustrates an example of relationships between the contents and the window. In an example of FIG. 9, a display time, a user ID, a screen ID, a window ID, a contents ID and a time section of the contents are included. According to such data, it is possible to grasp what contents are displayed on which window. The time section of the contents represents a position from the beginning of the contents, for example (e.g. time for watching, the number of pages or the like).

Figures 5, 10:
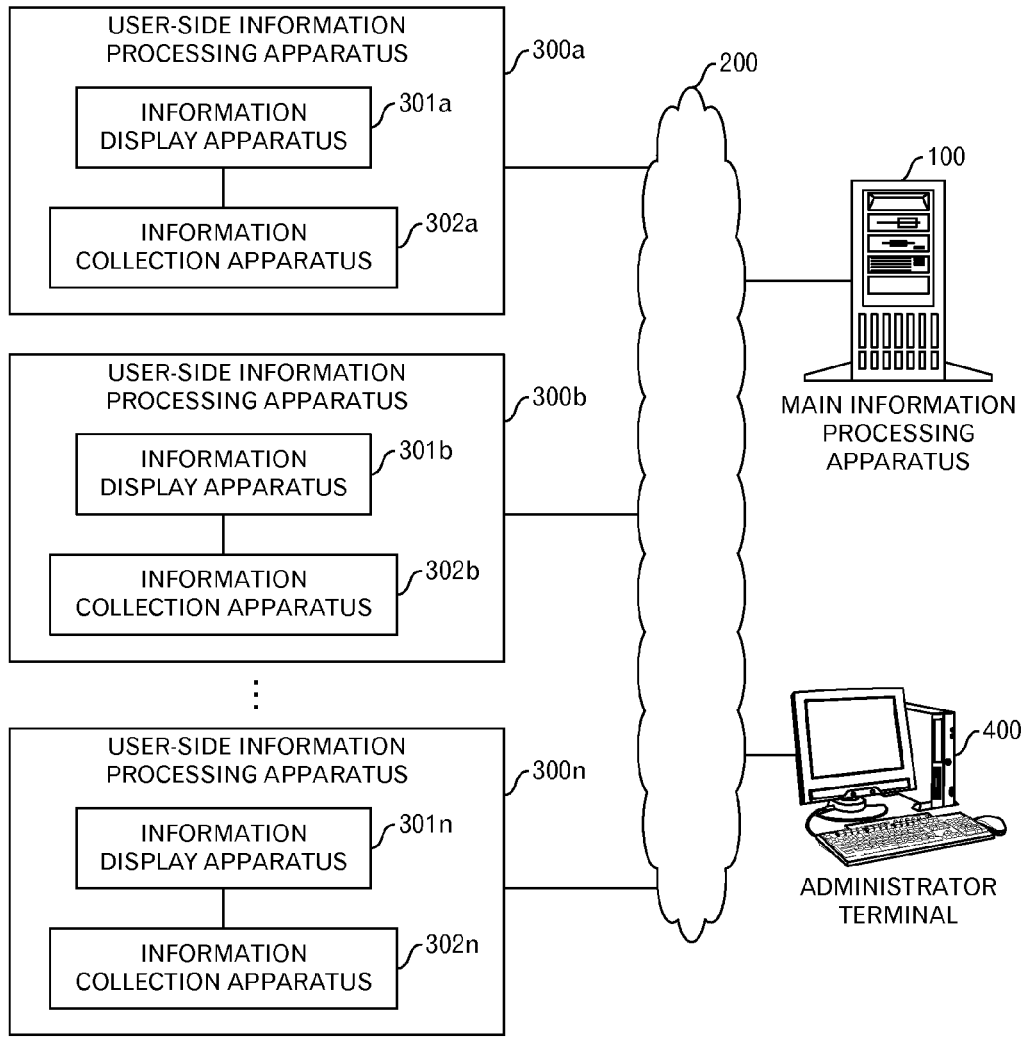
FIG. 5 is a diagram depicting an outline of a system relating to an embodiment of this invention.
FIG. 10 is a diagram depicting an example of data stored in the collected data storage unit.

FIG. 10 illustrates an example of storage destination data of the contents. In an example of FIG. 10, a contents ID and an address of the storage destination (Uniform Resource Identifier (URI)) are included. This data may be stored in advance.

Thus, for each user, data that represents that each window displayed on the display screen is displayed in what state and which contents are displayed in that window is stored as the history data.

Even when the contents are displayed on a window, the window may be hidden by other windows, and the user may not watch the contents in the window to be watched. Therefore, the history data of the window coordinates (FIG. 8) includes not only data representing the display position of the window and its display size but also the turn of that window in the depth direction of the screen.

Moreover, the eye position coordinate data obtained from the sensor data of the eye tracker is also stored in the collected data storage unit 102. FIG. 11 illustrates an example of the eye position coordinate data obtained as absolute coordinates on the display screen. In an example of FIG. 11, a measurement time, a user ID, a screen ID and x and y coordinate values are included.

On the other hand, when plural windows are displayed on the display screen, the eye position coordinate data within the window is calculated assuming that the window displayed foreground is watched considering the turns of the windows. In such a case, data as illustrated in FIG. 12 is stored in the collected data storage unit 102. In an example of FIG. 12, a measurement time, a user ID, a screen ID and x and y coordinate values are included. Relative coordinate values in the display screen are recorded.

In the following explanation, in order to simplify the explanation, an example that one window is displayed on the entire display screen, and the eye position coordinates are calculated as coordinates on the foreground window.

Returning to the explanation of the processing in FIG. 7, the transition identifying unit 103 determines whether or not the present time is a first timing for identifying the transition of the movement directions of the eye gaze (step S3). For example, whether or not the present time is a predetermined timing counted by a timer, or whether or not the present time is timing when all data is received from users to be compared is determined. When the present time is not the aforementioned first timing, the processing shifts to a processing in FIG. 23 through terminal A.

On the other hand, when the present time is the aforementioned first timing, the transition identifying unit 103 reads out the eye position coordinate data for the user to be processed in plural time periods to be processed from the collected data storage unit 102 (step S5).

Then, the transition identifying unit 103 identifies one unprocessed user in the read out eye position coordinate data (step S7). Then, the movement direction estimating unit 1031 performs a processing for estimating a movement direction for the identified user, and stores the processing result in the transition data storage unit 104 (step S9). This processing for estimating a movement direction will be explained by using FIGS. 13 to 19.

Figure 13:
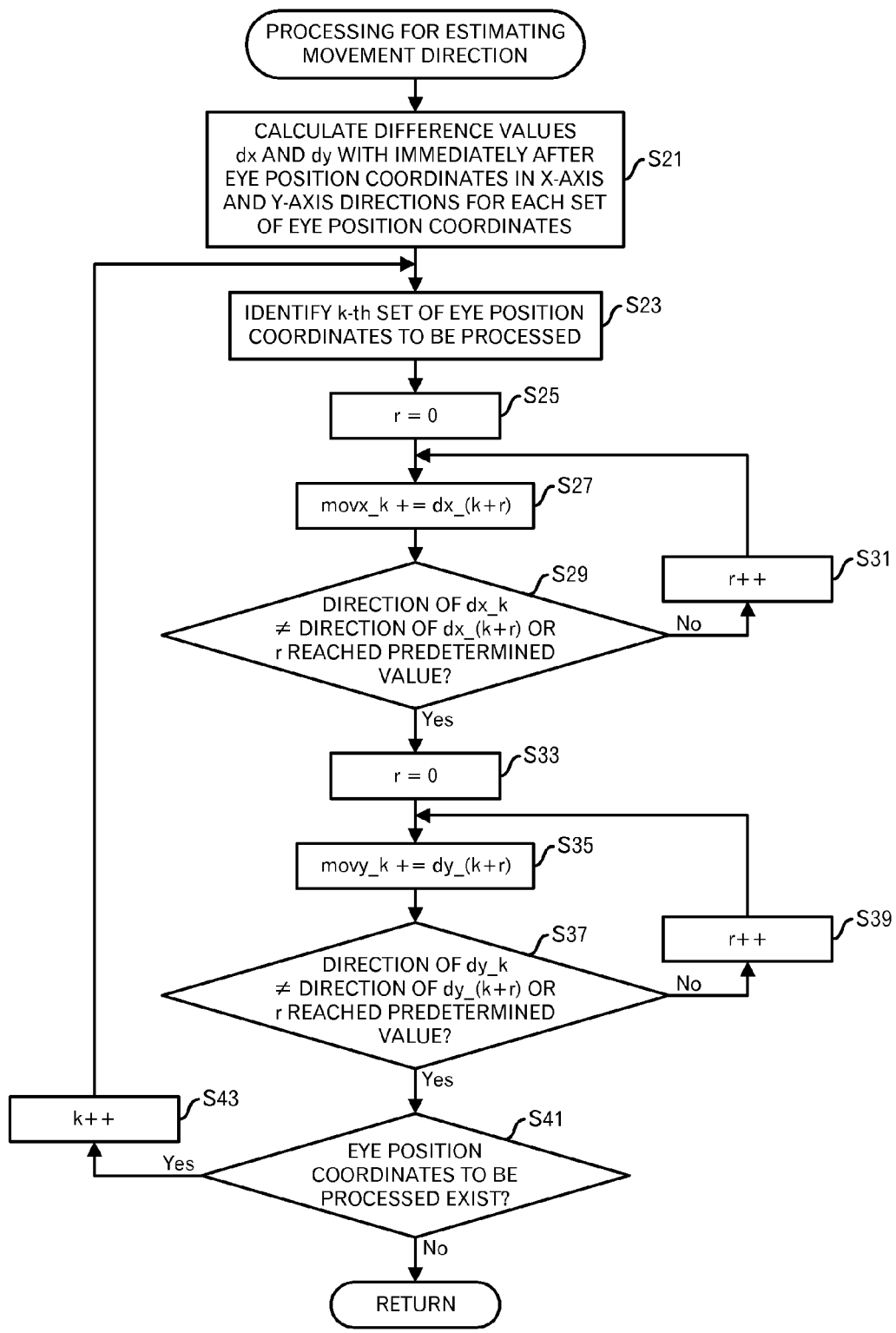
FIG. 13 is a diagram depicting a processing flow of a processing for estimating a movement direction.

Firstly, the movement direction estimating unit 1031 calculates, for each set of the eye position coordinates (except the last set of the eye position coordinates), difference values dx and dy with the eye position coordinates immediately after the eye position coordinates to be processed in the X-axis and the Y-axis directions (FIG. 13: step S21). For example, as for the X-axis direction, a difference $dx\_1$ between the first eye position coordinate and the second eye position coordinate, a difference $dx\_2$ between the second eye position coordinate and the third eye position coordinate, a difference $dx\_3$ between the third eye position coordinate and the fourth eye position coordinate, a difference $dx\_4$ between the fourth eye position coordinate and the fifth eye position coordinate a difference $dx\_5$ between the fifth eye position coordinate and the sixth eye position coordinate and a difference $dx\_6$ between the sixth eye position coordinate and the seventh eye position coordinate are calculated. As for the Y-axis direction, the same calculation is performed.

Moreover, the movement direction estimating unit 1031 identifies one set of the eye position coordinates to be processed (here, k-th set of the eye position coordinates) (step S23).

Then, the movement direction estimating unit 1031 initializes a variable r to "0" (step S25). After that, the movement direction estimating unit 1031 adds r-th difference $dx\_(k+r)$ to the substantial movement amount $movx\_k$ for the eye position coordinates k to be processed (step S27).

Then, the movement direction estimating unit 1031 determines whether or not the direction of $dx\_k$ is different from the direction of $dx\_(k+r)$, in other words, whether or not the direction of $dx\_(k+r)$ is reversed (i.e. the plus/minus sign of the $dx\_(k+r)$ is reversed) or whether or not r reached a predetermined value (which corresponds to a predetermined duration of time) (step S29).

When conditions at this step S29 are not satisfied, the movement direction estimating unit 1031 increments r by "1" (step S31) in order to accumulatively add $dx\_(k+r+1)$ to $movx\_k$, and the processing returns to the step S27.

On the other hand, when any condition at the step S29 is satisfied, the substantial movement amount for the eye position coordinates to be processed this time is obtained for the X-axis direction. Then, the movement direction estimating unit 1031 initializes the variable r to "0" (step S33). After that, the movement direction estimating unit 1031 adds the r-th difference $dy\_(k+r)$ to the substantial movement amount $movy\_k$ for the k-th set of the eye position coordinates to be processed (step S35).

Then, the movement direction estimating unit 1031 determines whether or not the direction of $dy\_k$ is different from the direction of $dy\_(k+r)$, in other words, whether or not the direction of $dy\_(k+r)$ is reversed (i.e. the plus/minus sign of the $dy\_(k+r)$ is reversed) or whether or not r reached a predetermined value (which corresponds to a predetermined duration of time) (step S37).

When conditions at this step S37 are not satisfied, the movement direction estimating unit 1031 increments r by "1" (step S39) in order to accumulatively add $dy\_(k+r+1)$ to $movy\_k$, and the processing returns to the step S35.

On the other hand, when any condition at the step S37 is satisfied, the substantial movement amount for the eye position coordinates to be processed this time is obtained for the Y-axis direction. Then, the movement direction estimating unit 1031 determines whether or not any eye position coordinates to be processed exist in the eye position coordinate data read out at the step S5 (step S41).

When there are eye position coordinates to be processed, the movement direction estimating unit 1031 increments k by "1" (step S43), and the processing returns to the step S23. On the other hand, when there are no residual eye position coordinates, the processing returns to the calling-source processing.

Figure 14:
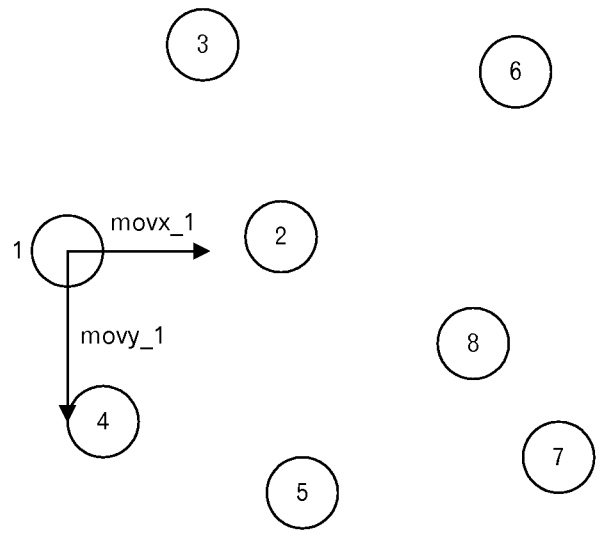
FIG. 14 is a diagram depicting an example of calculating the movement direction.
Figure 15:
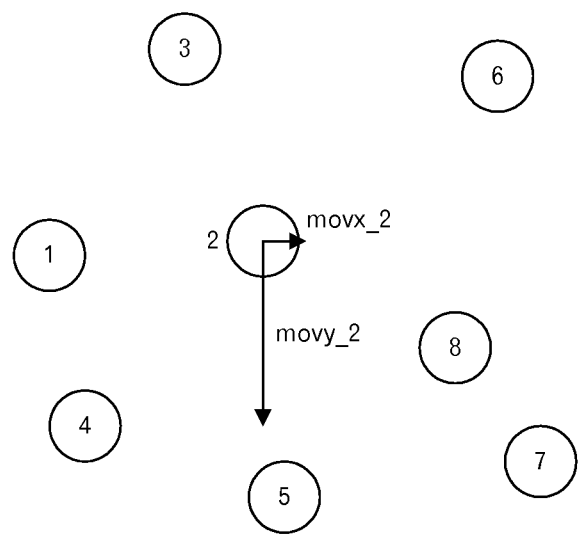
FIG. 15 is a diagram depicting an example of calculating the movement direction.
Figure 16:
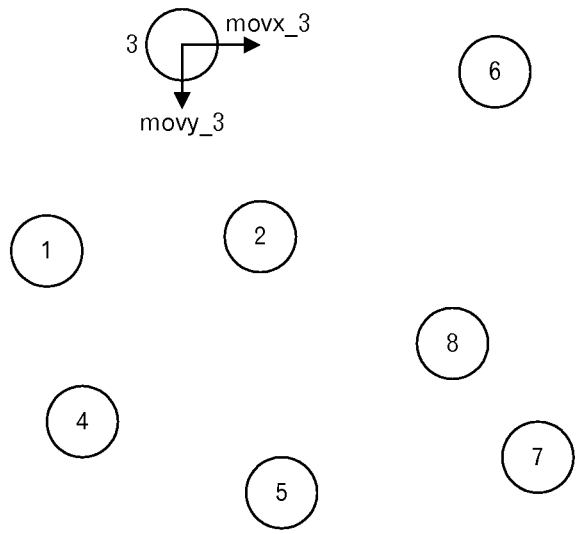
FIG. 16 is a diagram depicting an example of calculating the movement direction.
Figure 17:
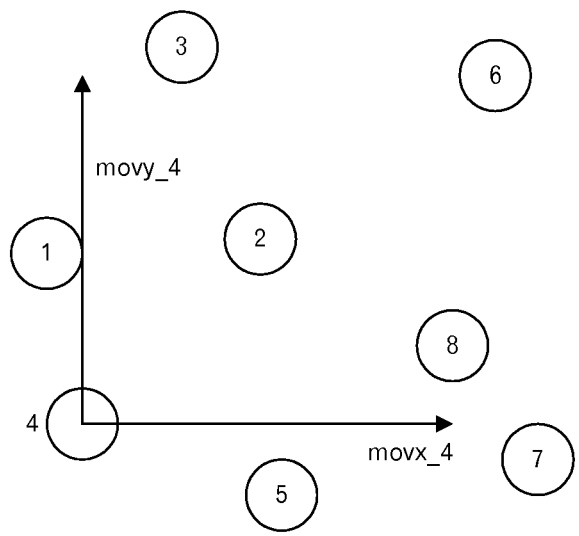
FIG. 17 is a diagram depicting an example of calculating the movement direction.
Figure 18:
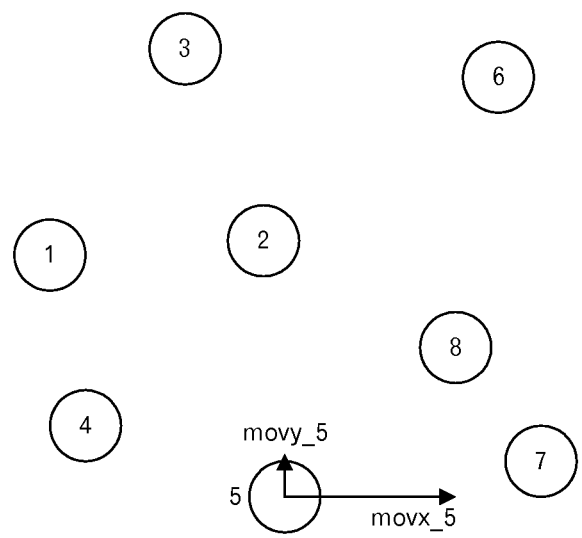
FIG. 18 is a diagram depicting an example of calculating the movement direction.
Figure 19:
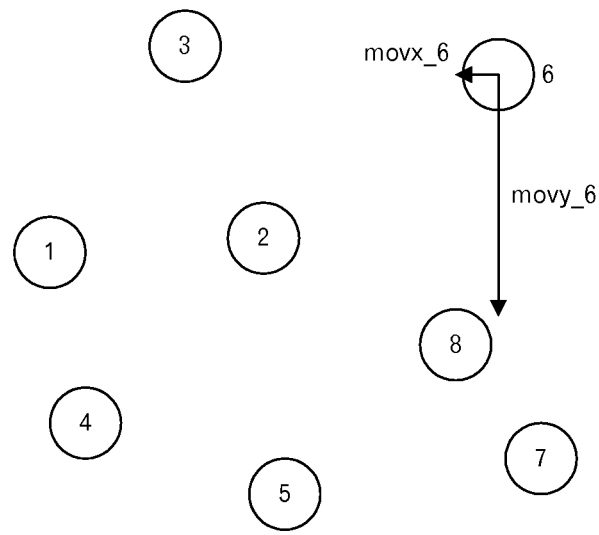
FIG. 19 is a diagram depicting an example of calculating the movement direction.

For example, in the example of FIG. 2, when the upper limit value of r is "6", movx and movy are obtained as illustrated in FIGS. 14 to 19. FIG. 14 illustrates movx_1 and movy_1. FIG. 15 illustrates movx_2 and movy_2. FIG. 16 illustrates movx_3 and movy_3. FIG. 17 illustrates movx_4 and movy_4. FIG. 18 illustrates movx_5 and movy_5. FIG. 19 illustrates movx_6 and movy_6.

Moreover, the processing results of the movement direction estimating unit 1031 are stored in the transition data storage unit 104. For example, data as illustrated in FIG. 20 is stored. In an example of FIG. 20, for each of the X-axis and Y-axis, the substantial movement amounts movx and movy are registered for each time from t=1 to t=6. The substantial movement amounts represent the directions of the X-axis and Y-axis by their plus/minus signs. As illustrated in FIGS. 14 to 19, in case of the X-axis direction, the positive substantial movement amount represents the right direction, and the negative substantial movement amount represents the left direction. In case of the Y-axis direction, the positive substantial movement amount represents the upward direction, and the negative substantial movement amount represents the downward direction.

Returning to the explanation of the processing in FIG. 7, the transition identifying unit 103 identifies a movement direction label of each time from the estimated movement direction calculated by the movement direction estimating unit 1031, and stores the processing result in the transition data storage unit 104 (step S11).

When the results as illustrated in FIG. 20 are obtained, data as illustrated in FIG. 21 is obtained. The right direction is represented by "R", the left direction is represented by "L", the upward direction is represented by "U", and the downward direction is represented by "D".

In this embodiment, when an absolute value of the substantial movement amount is equal to or less than 10, for example, it is assumed that the substantial movement amount is not detected as the error. Moreover, when the absolute value of the substantial movement amount is a value that exceeds the frame of the display screen (in the Y-axis direction, the value is equal to or greater than the height "Height", and in the X-axis direction, the value is equal to or greater than the horizontal width "width"), it is also assumed that the substantial movement amount is not detected, because the user watches an area other than the display screen.

Then, in FIG. 21, as for t=2 and t=6 in the X-axis direction and t=5 in the Y-axis direction, the absolute values of the substantial movement amounts are equal to or less than 10. Therefore, they are excluded, and are represented by "-". As for other lines, the labeling is performed according to the aforementioned rule. For convenience of explanation, no labeling is performed for t=7.

Furthermore, the transition identifying unit 103 aggregates, for each time period, the movement direction labels at each time, and stores the aggregation results in the transition data storage unit 104 (step S13). For example, when the time period is set for each two seconds, it is determined whether or not there is a type of label whose occurrence frequency is equal to or greater than a threshold (e.g. 60% or more) among labels (e.g. 7 labels) included in two seconds. When it is determined that there is the aforementioned label, the label is identified as a label that is representative of that time period, and when it is determined that there is not the aforementioned label, "-", which represents no label that is representative of that time period, is set.

For example, in the example of FIG. 21, as for the X-axis direction, a type of all of the labels is "R". Therefore, R is selected. As for the Y-axis direction, a type of 4 labels is "D" among 5 labels, therefore, D is selected. By performing the aforementioned determination for each time period, data as illustrated in FIG. 22 is obtained. In this example, the data as illustrated in FIG. 21 is aggregated as transition data of the time period of 2 seconds from the time 0 to 2 seconds in FIG. 22.

Then, the transition identifying unit 103 determines whether or not there is an unprocessed user in the collected data storage unit 102 (step S15). When there is an unprocessed user, the processing returns to the step S7. On the other hand, when there is no unprocessed user, the processing shifts to step S51 in FIG. 23 through terminal B.

Figure 23:
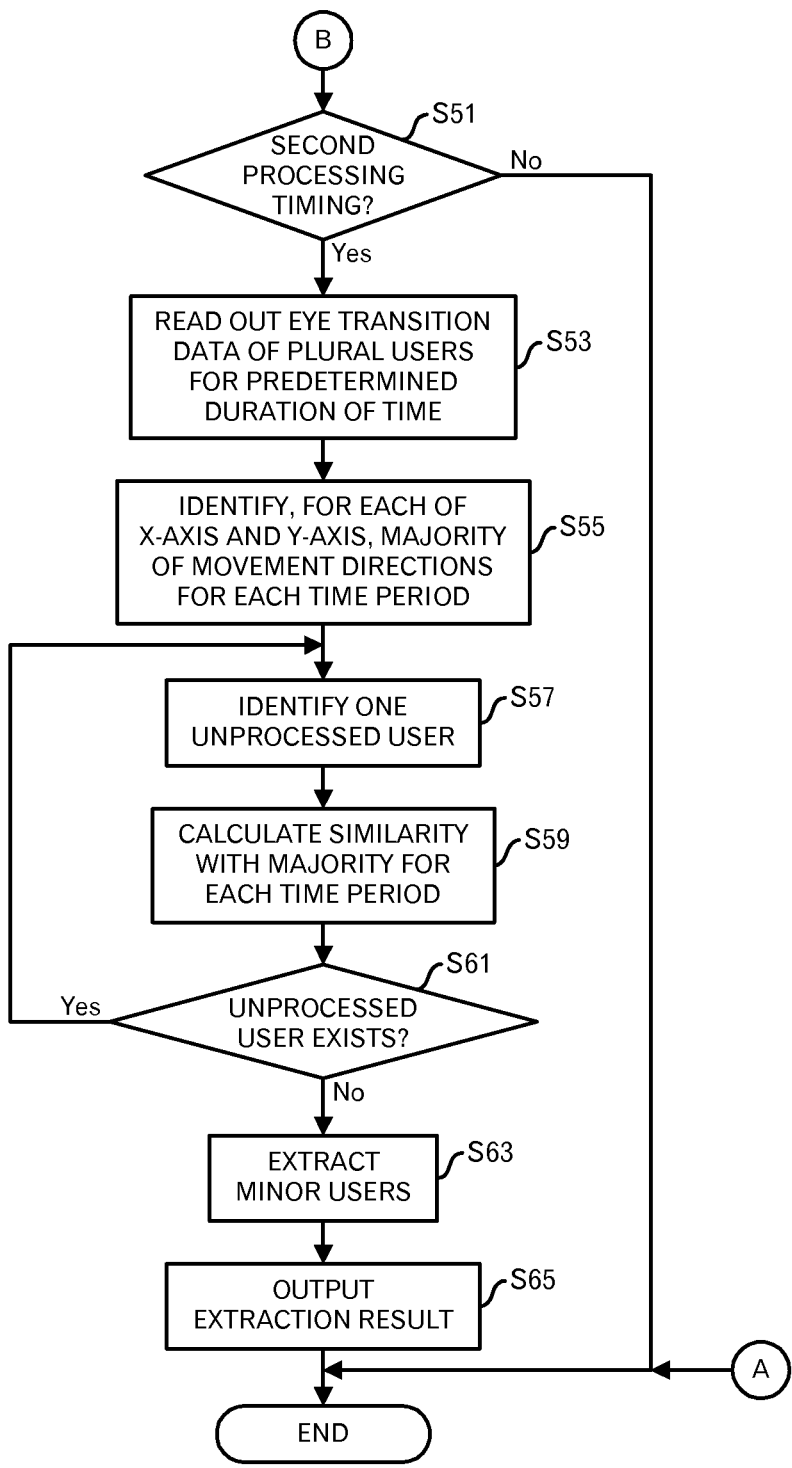
FIG. 23 is a diagram depicting a processing flow in the first embodiment.

Shifting to the step S51 in FIG. 23 through the terminal B, the extraction unit 105 determines whether or not the present time is a second timing for identifying the majority and minority (step S51). For example, whether or not the present time is a predetermined timing measured by a timer or whether or not the present time is timing when data to be processed has been prepared is determined. When the present time is not the aforementioned second timing, the processing ends.

On the other hand, when the present time is the second timing, the extraction unit 105 reads out the eye transition data of plural users for a predetermined duration of time including plural time periods (step S53).

Then, the majority determination unit 1051 of the extraction unit 105 determines, for each of the X-axis and Y-axis, the majority of the movement directions of the respective time period (step S55).

The majority determination will be explained by using FIG. 24. In an example of FIG. 24, for each of the X-axis and Y-axis and for each of n users, the movement direction label for each time period is listed. Then, at this step, for each time period, the movement direction label, which is selected for the greatest number of users, is determined as the majority of the movement direction. For example, as for the time period from the time 0 to 2 seconds, the number of users for which "R" is selected is greater for the X-axis. Therefore, "R" is identified as the majority. As for the Y-axis, the number of users, for which "D" is selected, is equal to the number of users, for which "U" is selected. Therefore, it is impossible to identify the majority, and "-", which represents no majority, is registered. When this processing is performed for each time period, the last line for the X-axis and the last line for the Y-axis are obtained.

After that, the minority extraction unit 1052 of the extraction unit 105 extracts one unprocessed user in the read out data (step S57). Then, the minority extraction unit 1052 calculates a similarity with the majority for each time period and for the identified user (step S59).

More specifically, for each time period, when the movement direction is identical with the movement direction of the majority, the similarity "1" is calculated, when the movement direction is not identical with the movement direction of the majority, the similarity "0" is calculated, and in case of other cases (e.g. either of the movement directions is "-"), the similarity "0.5" is calculated. In the example illustrated in FIG. 24, when this step is performed, the result as illustrated in FIG. 25 is obtained for the first user "UserR1". In this example, as for the X-axis, there is a lot of "1", however, as for the Y-axis, "1" is not major.

At this step, the average value or total sum of the similarities for the X-axis and the average value or total sum of the similarities for the Y-axis may be calculated to employ them as an overall similarity. Furthermore, after the average value for each time period or the like is calculated, an overall similarity may be calculated by the average or total sum.

Then, the minority extraction unit 1052 determines whether or not there is an unprocessed user in the read out data (step S61). When there is an unprocessed user, the processing returns to the step S57. On the other hand, when there is no unprocessed user, the minority extraction unit 1052 extracts users of the minority based on the calculated similarities, and stores data concerning the extracted users in the extracted data storage unit 106 (step S63). For example, a user whose overall similarity is less than a threshold may be identified as the minority, or a user whose number of time periods of the similarity "1" for the X-axis or Y-axis is less than a predetermined number may be identified as the minority.

After that, the output unit 107 transmits data of the minor users, which is stored in the extracted data storage unit 106, to the administrator terminal 400, for example (step S65). Accordingly, the administrator can identify users having any trouble. Alarm data may be transmitted to the user-side information processing apparatuses 300 of the minor users.

By repeating this processing periodically or in response to a request from the administrator or the like, users who made non-typical transition of the movement directions of the eye gaze can be identified.

According to this embodiment, even when the eye tracker with low accuracy is employed, the transition of the movement directions of the eye gaze is identified by extracting the movement directions of the eye gaze by a method that is appropriate for their characteristics, and it becomes possible to identify the majority and minority of the users.

Thus, it is possible to detect the partial omission of the document check task or the skip of the important parts in the online education, and suppress them.

Embodiment 2

In this embodiment, a method for extracting the minor users, which is different from that of the first embodiment, is employed. However, the outline of the system illustrated in FIG. 5 is similar to that of this embodiment.

Figure 26:
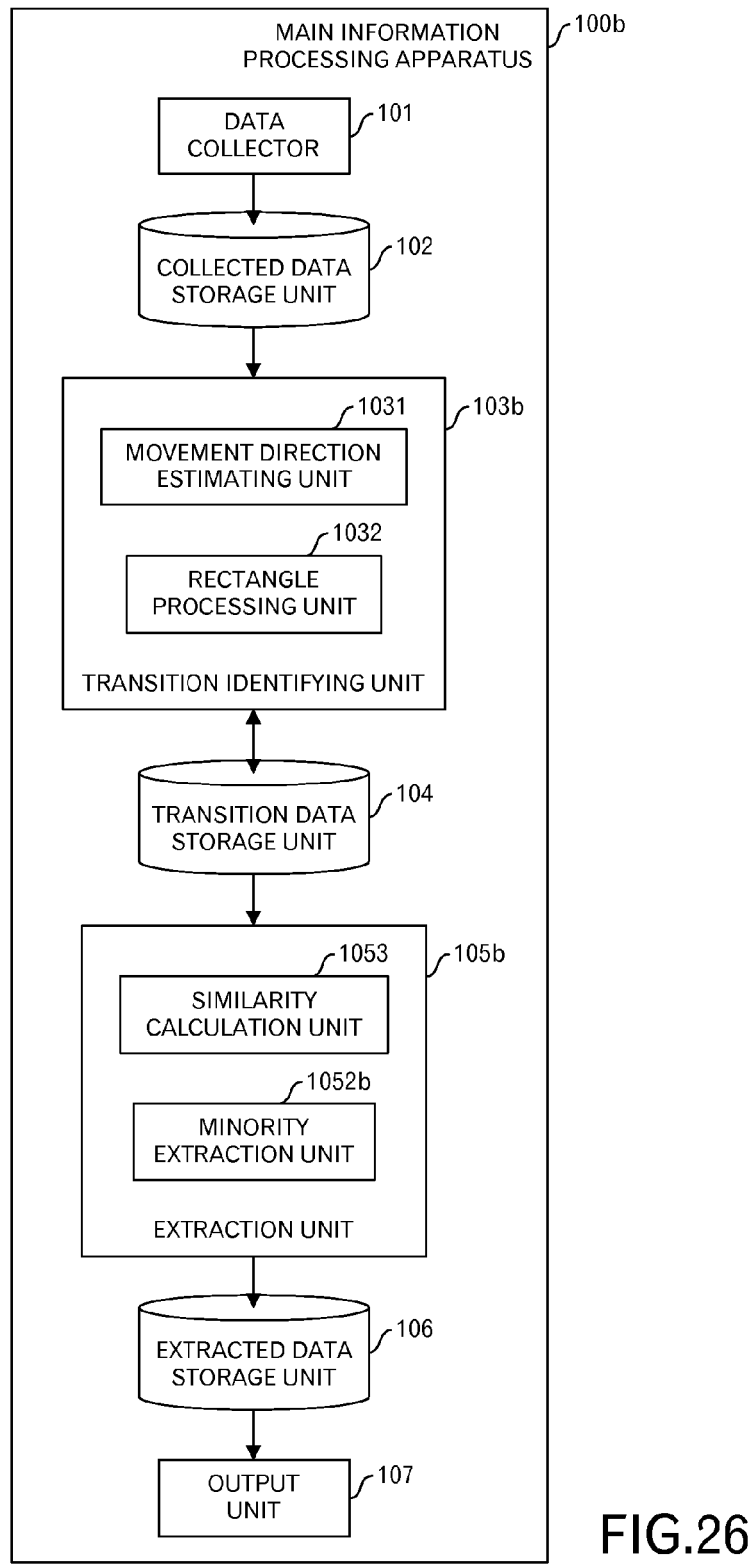
FIG. 26 is a functional block diagram of a main information processing apparatus in a second embodiment.

FIG. 26 illustrates a configuration example of a main information processing apparatus 100b relating to this embodiment.

The basic configuration of the main information processing apparatus 100b relating to this embodiment is similar to that of the first embodiment, and the configurations of the transition identifying unit 103b and the extraction unit 105b are different.

In other words, the transition identifying unit 103b has a rectangle processing unit 1032 in addition to the movement direction estimating unit 1031. The rectangle processing unit 1032 performs a processing to numeralize the transition of the movement directions of the eye gaze for each time period.

Moreover, the extraction unit 105b has a similarity calculation unit 1053 and a minority extraction unit 1052b. The similarity calculation unit 1053 calculates, for each user, a similarity between the user and another user, based on the processing results of the rectangle processing unit 1032.

The minority extraction unit 1052b extracts the minor users based on the similarities calculated by the similarity calculation unit 1053.

Next, processing contents of the main information processing apparatus 100b relating to this embodiment will be explained by using FIGS. 27 to 32.

Figure 27:
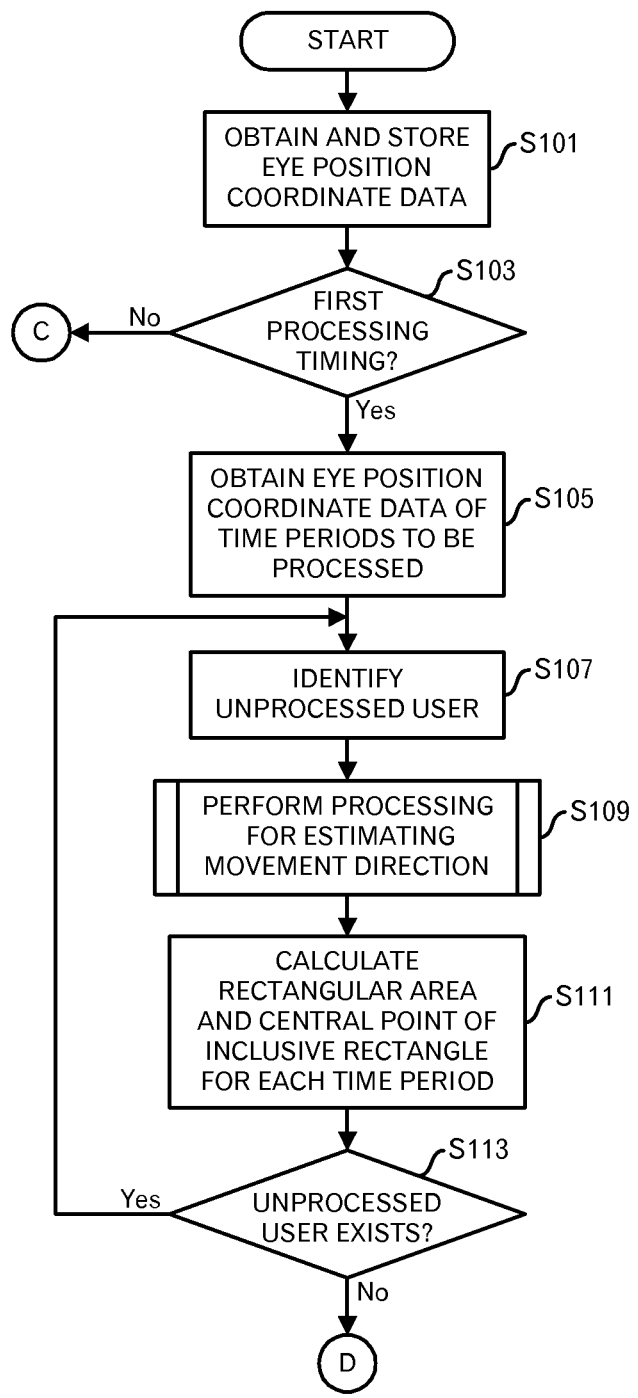
FIG. 27 is a diagram depicting a processing flow in the second embodiment.

Firstly, the data collector 101 receives sensor data, display history data and the like from the respective user-side information processing apparatuses 300a to 300n, converts the sensor data into the eye position coordinate data, and stores the eye position coordinate data in the collected data storage unit 102 (FIG. 27: step S101). This step is the same as the step S1.

Next, the transition identifying unit 103b determines whether or not the present time is a first timing for identifying the transition of the movement directions of the eye gaze (step S103). This step is the same as the step S3. When the present time is not the aforementioned first timing, the processing shifts to a processing in FIG. 31 through terminal C.

On the other hand, when the present time is the aforementioned first timing, the transition identifying unit 103b reads out the eye position coordinate data within plural time periods to be processed for the users to be processed from the collected data storage unit 102 (step S105). This step is the same as the step S5.

Then, the transition identifying unit 103b identifies one unprocessed user in the read out eye position coordinate data (step S107). This step is the same as the step S7. Then, the movement direction estimating unit 1031 performs the processing for estimating the movement direction for the identified user, and stores the processing results in the transition data storage unit 104 (step S109). This processing for estimating the movement direction is the same as that illustrated in FIG. 13.

Then, the rectangle processing unit 1032 calculates a rectangular area of an inclusive rectangle that contains eye position coordinates and a movement direction at the eye position coordinates (the substantial movement amounts of the X-axis and Y-axis) and coordinate values of the central point of the inclusive rectangle (or either of them), and stores the calculated data in the transition data storage unit 104 (step S111).

Figure 28:
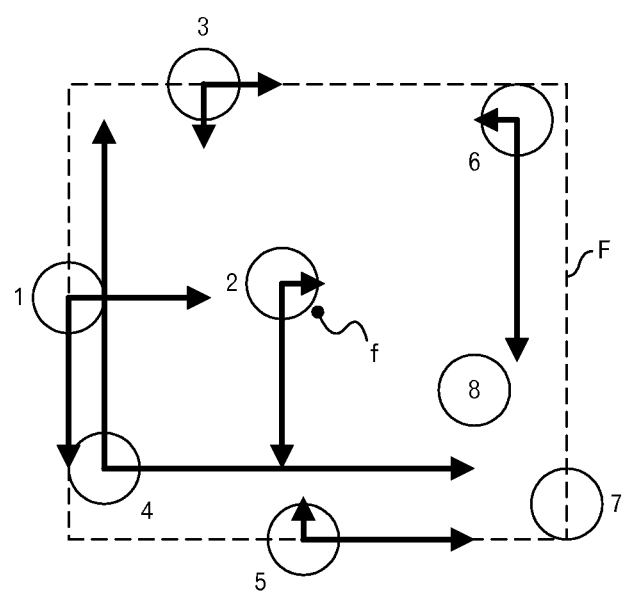
FIG. 28 is a diagram depicting an example of an inclusive rectangle.
Figure 29:
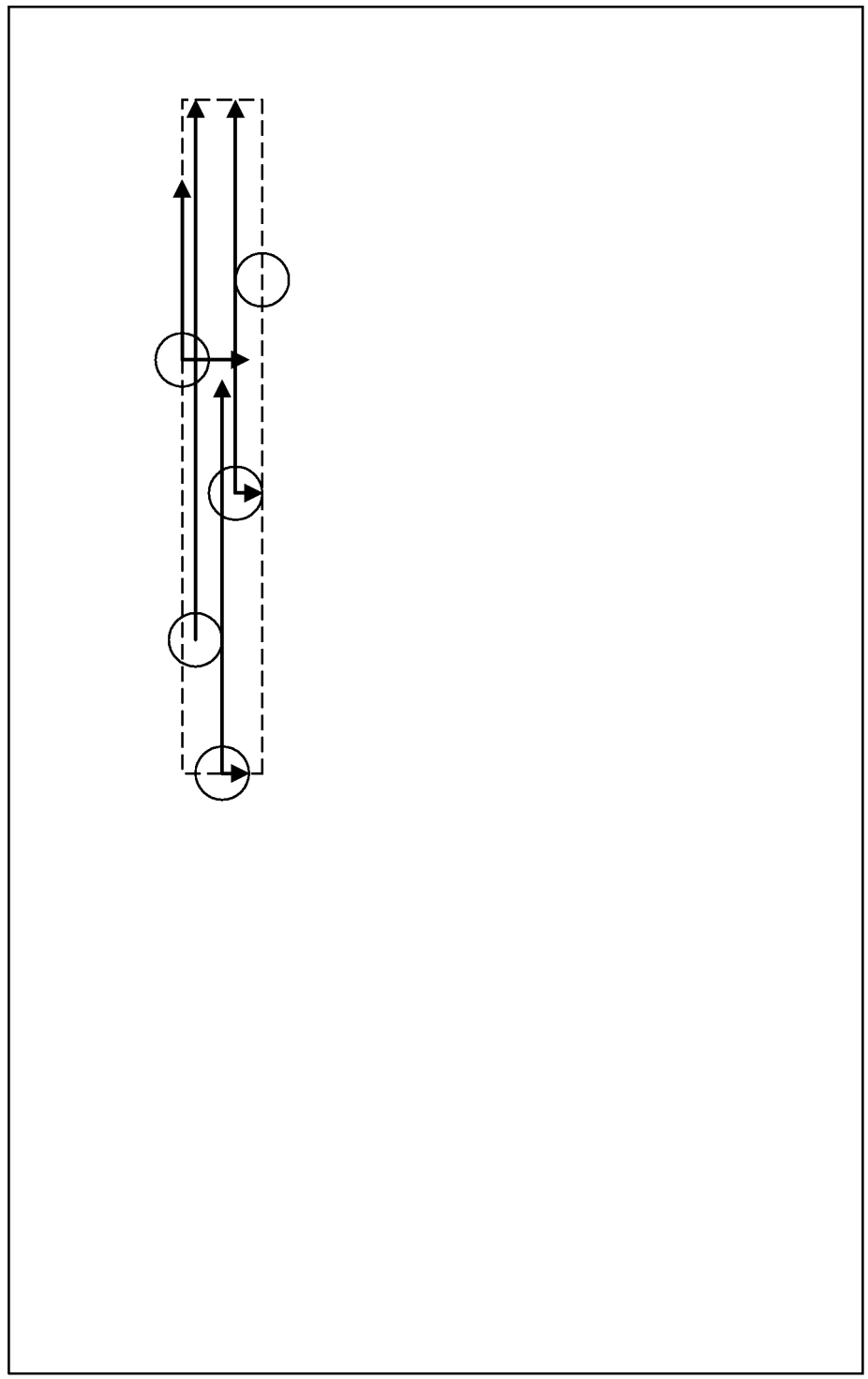
FIG. 29 is a diagram depicting another example of the inclusive rectangle.

For example, in the example of FIG. 2, an inclusive rectangle F is identified as illustrated in FIG. 28. The central point of the inclusive rectangle F is a point f. Thus, in a state that the user gazes steadily on a certain area, the rectangle is almost identical to the inclusive rectangle of the eye position. However, in a time period when the eye moves largely as illustrated in (b) of FIG. 1, a shape of the inclusive rectangle is determined by the coordinates of the movement destination, which corresponds to the movement direction from the eye position as illustrated in FIG. 29. An outer frame in FIG. 29 represents an outer shape of the display area in case of the screen illustrated in the same direction as that of (b) in FIG. 1.

Then, data as illustrated in FIG. 30 is stored in the transition data storage unit 104. In the example of FIG. 30, a rectangular area of the inclusive rectangle and the coordinates of the central point of the inclusive rectangle are stored for each user and each time period.

Then, the transition identifying unit 103b determines whether or not there is an unprocessed user in the data read out at the step S105 (step S113). When there is an unprocessed user, the processing returns to the step S107. On the other hand, when there is no unprocessed user, the processing shifts to a processing in FIG. 31 through terminal D.

Figure 31:
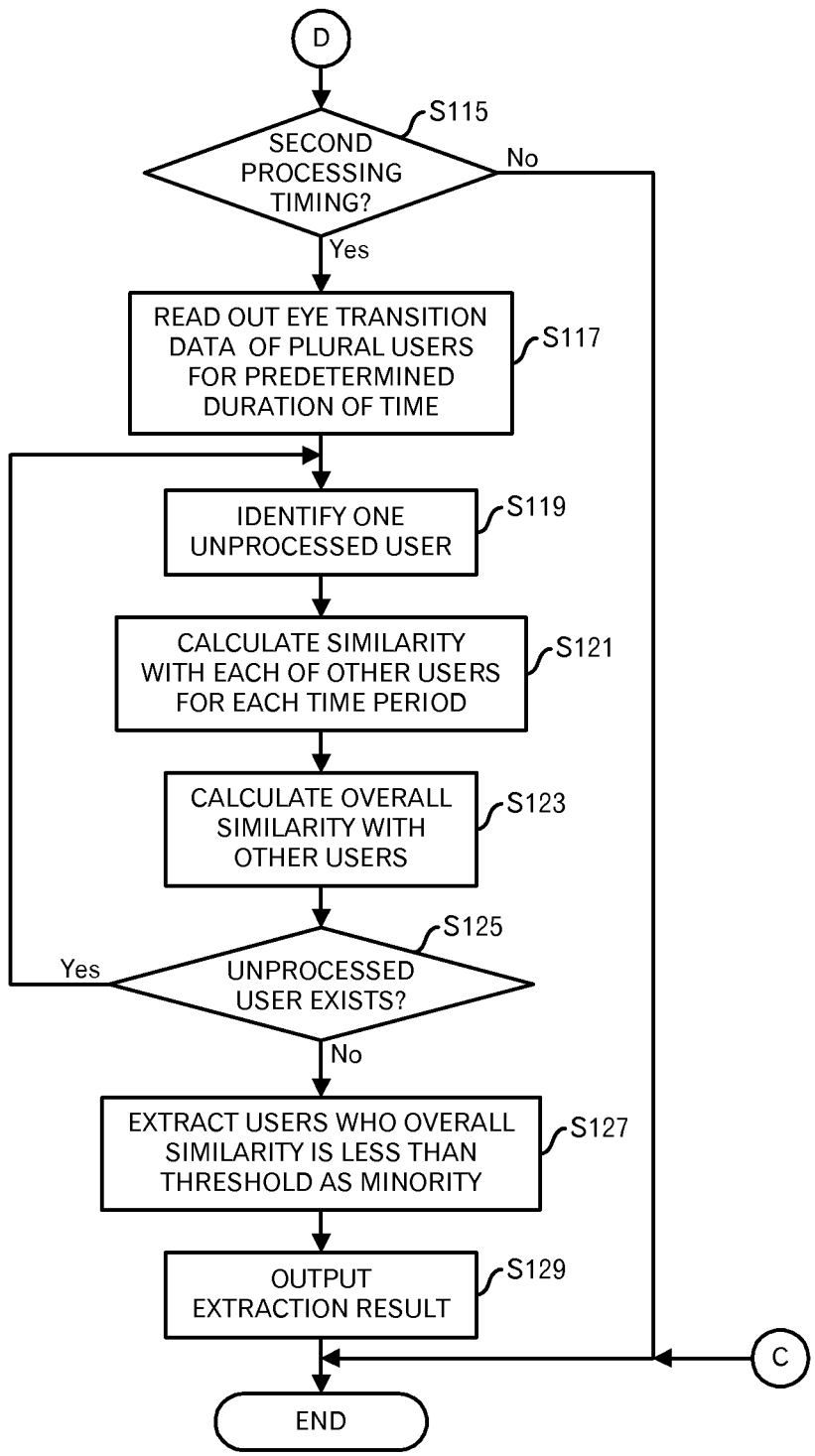
FIG. 31 is a diagram depicting a processing flow in the second embodiment.

Shifting to the explanation of the processing in FIG. 31, the extraction unit 105b determines whether or not the present time is a second timing for identifying the majority and minority (step S115). This step is the same as the step S51. When the present time is not the aforementioned second timing, the processing ends.

On the other hand, when the present time is the second timing, the extraction unit 105b reads out the eye transition data for a predetermined duration of time including plural time period for plural users (step S117).

Then, the similarity calculation unit 1053 identifies one unprocessed user in the data read out at the step S117 (step S119). Moreover, the similarity calculation unit 1053 calculates, for each time period, a similarity with each of other users (step S121).

For example, the similarity of the rectangular area of the inclusive rectangle is calculated as follows:

$$1-|(\text{rectangular area of first user})-(\text{rectangular area of second user})|/(\text{reference area for normalization})$$

The first user corresponds to the user identified at the step S119. As for the reference area for the normalization, the same value may be employed for all users, or the rectangular area of the first user may be employed.

Furthermore, the similarity for the central point of the inclusive rectangle is calculated by $\{1-(\text{normalized distance between central points})\}$. The normalized distance between the central points is calculated, for example, as follows:

$$\{((x \text{ coordinate value of first user})-(x \text{ coordinate value of second user}))^2 + ((y \text{ coordinate value of first user})-(y \text{ coordinate value of second user}))^2\}^{0.5}/(\text{reference distance for normalization})$$

The reference distance for the normalization is a diagonal distance of the screen, for example. In case of a screen having 1600*1200 pixels, the diagonal distance is 2000 pixels.

Figures 32, 33, 34:
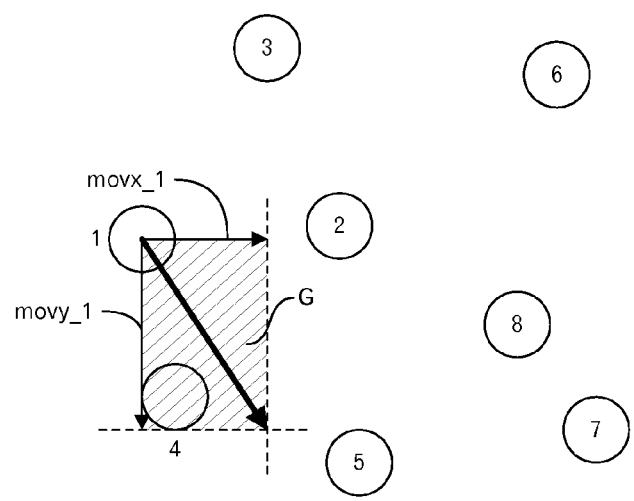
FIG. 32 is a diagram depicting an example of calculation of similarities in the second embodiment.
FIG. 33 is a diagram to explain a case where a rectangle identified from the movement direction is considered.
FIG. 34 is a diagram depicting an example of adjustment of the substantial movement amount.

For example, FIG. 32 illustrates an example that the similarity with each of other users for the time period 0-2 seconds is calculated, in the example of FIG. 30, for each user and for each of the rectangular area and the central point of the inclusive rectangle. As illustrated in FIG. 32, not only the individual similarities with each of other users but also the similarities with all other users are calculated. The similarity with all other users may be calculated as an average value of the similarities with each of other users. Moreover, the similarities for the rectangular area of the inclusive rectangle and the similarities for the central point of the inclusive rectangle are averaged to calculate the similarity with all other users.

Then, data as illustrated in FIG. 32 is generated for each time period.

Moreover, the similarity calculation unit 1053 calculates an overall similarity with other users (step S123). More specifically, the similarities with all other users, which are calculated for respective time periods, may be averaged with respect to plural users, or the minimum value may be employed among the similarities with all other users, which are calculated for respective users. Furthermore, the overall similarity may be calculated for each of the rectangular area of the inclusive rectangle and the central point of the inclusive rectangle, or one overall similarity calculated, for example, by using the average value of them may be calculated.

Then, the similarity calculation unit 1053 determines whether or not there is an unprocessed user in the data read out at the step S117 (step S125). When there is an unprocessed user, the processing returns to the step S119.

On the other hand, when there is no unprocessed user, the minority extraction unit 1052b extracts users whose overall similarity is less than a threshold as the minority, and stores the extraction results in the extracted data storage unit 106 (step S127). For example, when the overall similarity for the rectangular area of the inclusive rectangle is less than a first threshold, or when the overall similarity for the central point is less than a second threshold, the user may be extracted as the minor user. Furthermore, in case where an integrated similarity of the overall similarities for the rectangular area and central point is calculated, when the integrated similarity is less than a third threshold, the user may be extracted as the minor user.

Furthermore, the major users may be extracted.

After that, the output unit 107 transmits data of the minor users, which is stored in the extracted data storage unit 106, to the administrator terminal 400, for example (step S129). Hence, the administrator can identify problematic users. Alarm data may be transmitted to the user-side information processing apparatuses 300 of the minor users.

By repeating the processing periodically or in response to a request from the administrator or the like, it becomes possible to identify users who made the non-typical transition of the movement directions of the eye gaze.

By performing the aforementioned processing, even when using an eye tracker with low accuracy, the transition of the movement directions of the eye gaze is identified by extracting the movement directions of the eye gaze using a method corresponding to that characteristic, and the majority and the minority are identified based on estimation by similarities.

Other Embodiments

In the second embodiment, the inclusive rectangle is defined so as to contain the eye position coordinates in the time period to be focused on and the movement direction at the eye position coordinates (the substantial movement amounts for the X-axis and Y-axis directions). However, other definition may be employed.

For example, the inclusive rectangle is defined so as to contain the eye position coordinates and a rectangle identified by the substantial movement amount movx in the X-axis direction and the substantial movement amount movy in the Y-axis direction. This is because such a rectangle is handled as a movement range of the eye gaze.

As schematically illustrated in FIG. 33, a rectangle G that has a horizontal width movx_1 and a vertical width movy_1 is identified. Such a rectangle is generated for each eye position in the time period to be focused on, and the inclusive rectangle that contains those rectangles is identified.

Moreover, in case where movx_1 and movy_1 are obtained as illustrated in FIG. 20, the absolute value of the substantial movement amount is equal to or less than 10, it is assumed that the substantial movement amount is not detected as described above. Moreover, when the absolute value of the substantial movement amount is a value that represents the eye moves over the frame of the display screen (in the Y-axis direction, the value is equal to or greater than the height "Height" and in the X-axis direction, the value is equal to or greater than the horizontal width "width"), it is assumed that the user watches an area other than the display screen. Therefore, in this case, the substantial movement amount is excluded.

That is not all. When the movement that is equal to or longer than a detection error rad (a radius of a circle in FIG. 2) of the eye gaze occurs, it is possible to determine the apparent movement of the eye gaze. Therefore, the processing to identify the transition of the movement direction of the eye gaze, which is performed in the embodiments, may be redundant in view of identifying the movement direction. Therefore, when a value that is equal to or greater than rad (e.g. 300) is calculated as movx or movy, rad may be employed.

Then, the results in FIG. 20 are changed to those in FIG. 34. The inclusive rectangle may be identified as described in the second embodiment by employing those in FIG. 34 or the inclusive rectangle may be identified by employing the aforementioned new definition.

Furthermore, the reliability of the time period may be calculated based on the number of movx and movy, which are employed in that processing.

In FIG. 34, 7 values are calculated for only 6 time intervals among time intervals, which are identified by the 8 eye positions included in the time 0-2 seconds. However, in the X-axis direction, 4 points are employed among 6 points, and in the Y-axis direction, 5 points are employed among 6 points. Therefore, the reliability of the X-axis direction is ⅔, and the reliability of the Y-axis direction is ⅚. The reliabilities of the X-axis and Y-axis may be averaged.

The reliability may be reflected to the size of a rectangle identified by movx and movy. For example, a rectangle to which the reliability is reflected is arranged at the center of the rectangle identified by movx and movy.

Figure 35:
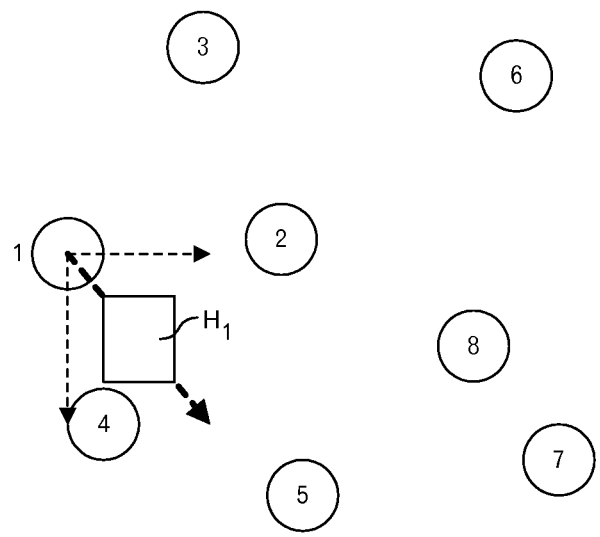
FIG. 35 is a diagram depicting an example of a rectangle for which a reliability is reflected.
Figure 36:
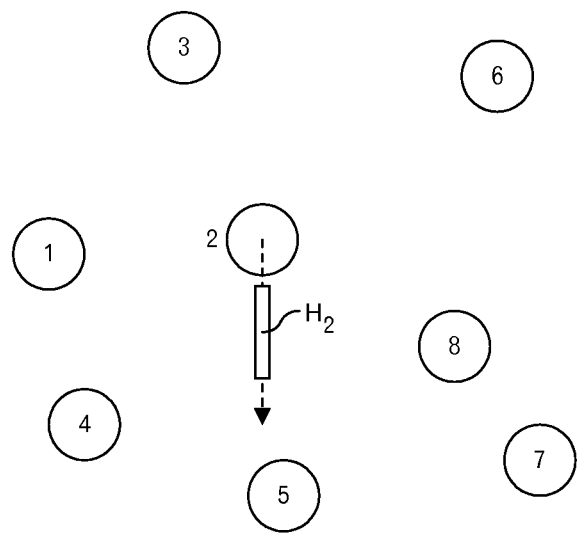
FIG. 36 is a diagram depicting an example of a rectangle for which the reliability is reflected.
Figure 37:
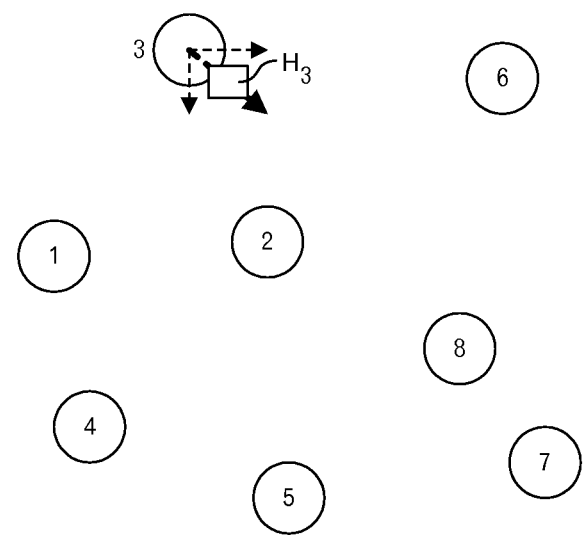
FIG. 37 is a diagram depicting an example of a rectangle for which the reliability is reflected.
Figure 38:
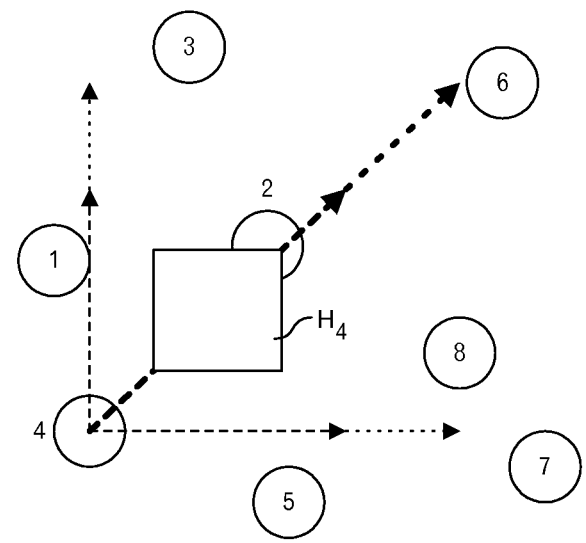
FIG. 38 is a diagram depicting an example of a rectangle for which the reliability is reflected.
Figure 39:
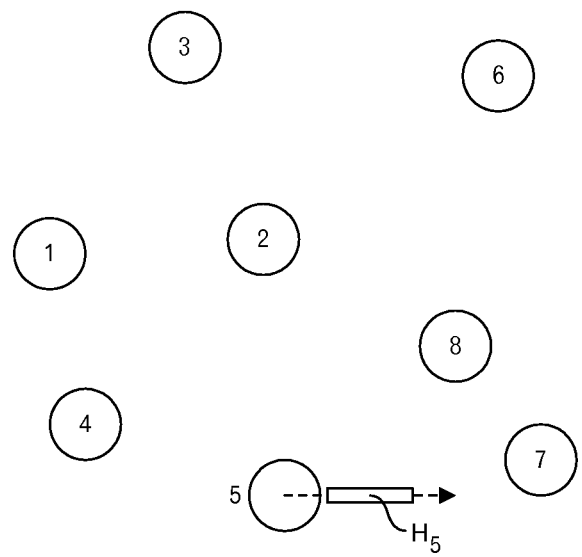
FIG. 39 is a diagram depicting an example of a rectangle for which the reliability is reflected.
Figure 40:
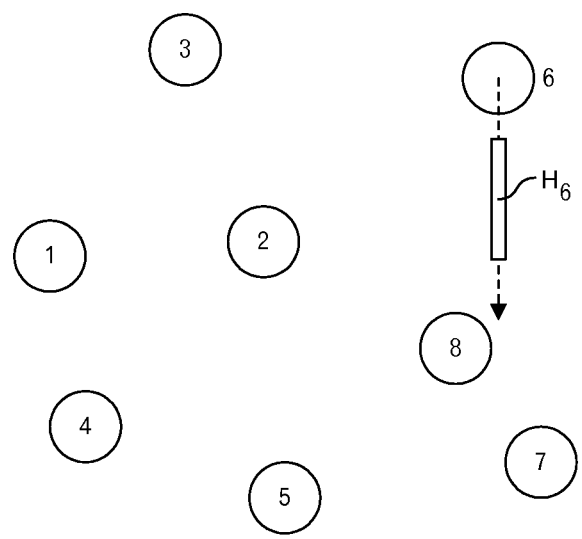
FIG. 40 is a diagram depicting an example of a rectangle for which the reliability is reflected.

In the example of FIG. 34, in case where the reliability is ½ for convenience, a rectangle $H_1$ as illustrated in FIG. 35 is obtained for a first eye position. Moreover, as illustrated in FIG. 36, as for a second eye position, because movx is excluded in the X-axis direction, the rectangle $H_2$ that is a substantial segment is obtained. As for a third eye position, a rectangle $H_3$ as illustrated in FIG. 37 is obtained. Moreover, as for a fourth eye position, as illustrated in FIG. 38, original movx and movy are shortened, and by reflecting the reliability to the shortened movx and movy, a rectangle $H_4$ is obtained. As for a fifth eye position, as illustrated in FIG. 39, movy is excluded in the Y-axis direction. Therefore, a rectangle $H_5$ that is a substantial segment is obtained. Similarly, as illustrated in FIG. 40, as for a sixth eye position, movx is excluded in the X-axis direction. Therefore, a rectangle $H_6$ that is a substantial segment is obtained.

Figure 41:
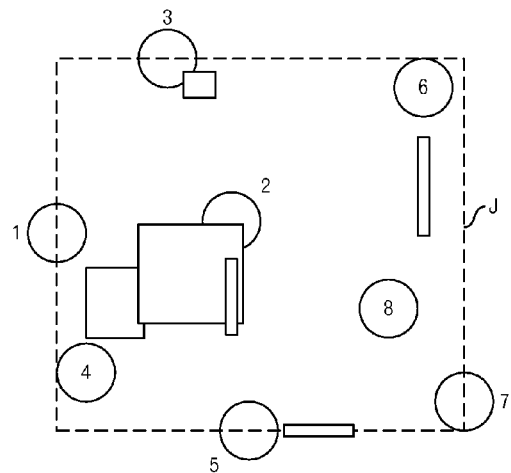
FIG. 41 is a diagram depicting an example of an inclusive rectangle in other embodiments.

Then, an inclusive rectangle J illustrated in FIG. 41 is obtained. In this example, the same results as that of FIG. 28 is obtained, however, the same results are not obtained for all cases.

Figure 42:
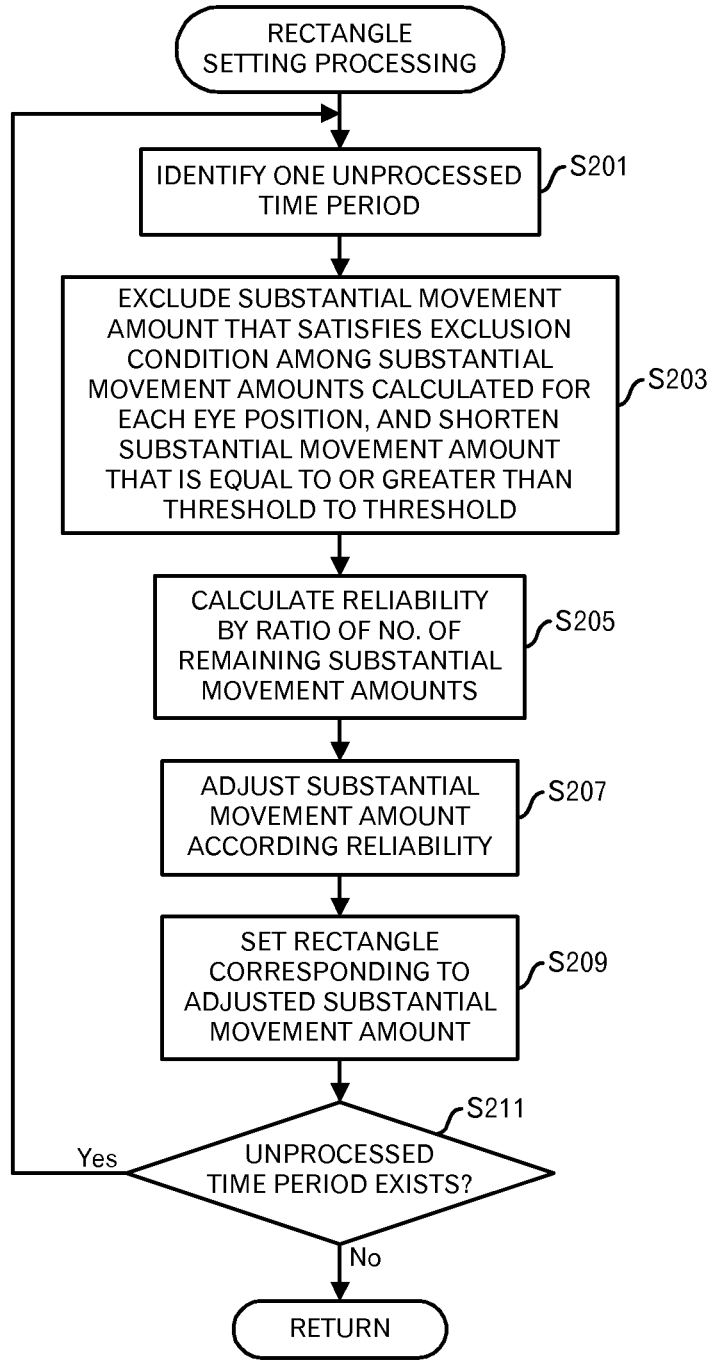
FIG. 42 is a diagram depicting a processing flow of a rectangle setting processing in other embodiments.

A setting processing of the rectangle using the reliability is summarized in FIG. 42. This processing is executed by the rectangle processing unit 1032 as a portion of the step S111.

For example, the rectangle processing unit 1032 identifies one unprocessed time period (step S201). Then, the rectangle processing unit 1032 excludes substantial movement amounts that satisfy an exclusion condition among the substantial movement amounts calculated for respective eye positions included in the identified time period, and shortens the substantial movement amounts that is equal to or greater than the threshold (the aforementioned rad) to the threshold (step S203).

The rectangle processing unit 1032 calculates a reliability by a ratio of the number of remaining substantial movement amounts to the number of substantial movement amounts (step S205). Furthermore, the rectangle processing unit 1032 adjusts the substantial movement amount according to the reliability (step S207). Then, the rectangle processing unit 1032 locates a rectangle corresponding to the adjusted substantial movement amount on the center of the rectangle identified by the substantial movement amount before the adjustment (step S209). The location of the rectangle is a mere example, and the rectangle may be located according to the eye position.

After that, the rectangle processing unit 1032 determines whether or not there is an unprocessed time period (step S211). When there is an unprocessed time period, the processing returns to the step S201. On the other hand, when there is no unprocessed time period, the processing returns to the calling-source processing.

The respective rectangles and inclusive rectangles may be used to identify a visual area and change of the visual areas as an area in which the possibility that the eye exists is high, instead of one parameter to extract the minor users. Moreover, by recording a flow of the eye gaze of the user who belongs to the majority and minority in time series and by reproducing the record later, the visual area and the change of the visual areas are used for logging or a log confirmation method of states for the document check task and/or the online education.

Although the embodiments of this invention were explained, this invention is not limited to those. For example, the configuration examples of the main information processing apparatuses 100 and 100b do not correspond to a program module configuration. Moreover, as for the processing flows, as long as the processing results do not change, the turns of the processing may be exchanged or plural steps may be executed in parallel.

Furthermore, the functions of the main information processing apparatus 100 or 100b may be shared by plural computers instead of one computer. As described above, the functions of the user-side information processing apparatus 300 and the main information processing apparatus 100 or 100b may be shared.

Figure 43:
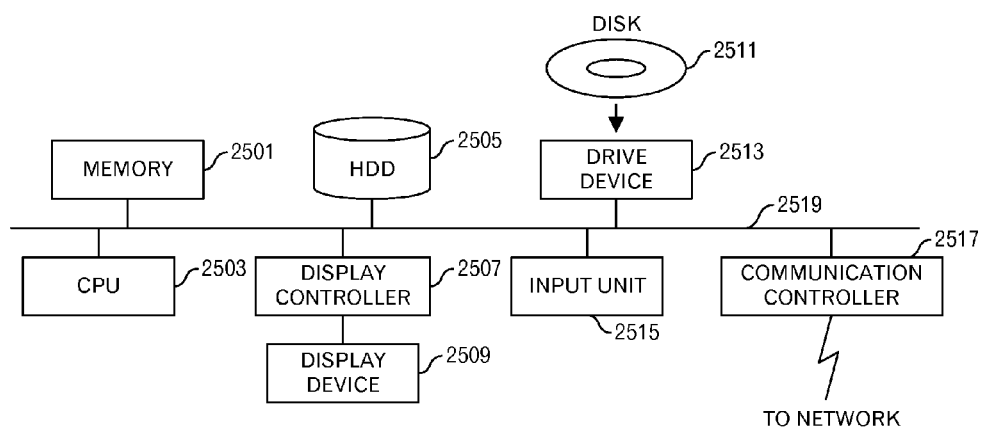
FIG. 43 is a functional block diagram of a computer.

In addition, the aforementioned main information processing apparatuses 100 and 100b are computer devices as shown in FIG. 43. That is, a memory 2501 (storage device), a CPU 2503 (processor), a hard disk drive (HDD) 2505, a display controller 2507 connected to a display device 2509, a drive device 2513 for a removable disk 2511, an input unit 2515, and a communication controller 2517 for connection with a network are connected through a bus 2519 as shown in FIG. 43. An operating system (OS) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform necessary operations. Besides, intermediate processing data is stored in the memory 2501, and if necessary, it is stored in the HDD 2505. In this embodiment of this technique, the application program to realize the aforementioned functions is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the necessary application programs systematically cooperate with each other, so that various functions as described above in details are realized.

The aforementioned embodiments are outlined as follows:

An information processing apparatus relating to this embodiment includes: (A) an identifying unit to identify, for each of plural users, transition of movement directions of an eye gaze of the user, from movement history of the eye gaze of the user on a display screen; and (B) an extraction unit to extract a minor user among the plural users based on the transition of the movement directions of the eye gaze, which is identified for each of the plural users.

Accordingly, when a user who partially forgets a document check task or skips reading of important portions in an online education is a minor user, it is possible to extract that minor user, and further alert and/or notify the minor user.

Moreover, the aforementioned extraction unit may (b1) compare, for each time period, the transition of the movement directions of the eye gaze among the plural users to identify transition of movement directions of the eye gaze, which is presumed to be a majority of the plural users; and (b2) extract a user whose transition of the movement directions of the eye gaze is dissimilar to the identified transition of the movement directions of the eye gaze. By identifying a reference transition of movement directions of the eye gaze for each time period, the minority is easily identified.

Furthermore, the aforementioned extraction unit may (b3) calculate, for each of the plural user, a similarity by comparing the transition of the movement directions of the eye gaze of the user with transition of movement directions of eye gaze of other users; and (b4) determine, for each of the plural user and based on the similarity calculated for the user, whether the user is a minor user. By calculating the similarity for other users as a numerical value, it is possible to extract the minor user.

Furthermore, the aforementioned identifying unit may calculate, for each eye position, a substantial movement amount within a predetermined duration of time from the eye position. On the other hand, the aforementioned identifying unit may calculate, for each eye position, an accumulated movement amount from the eye position to an eye position for which transition of a direction is detected within a predetermined duration of time, for each axis direction on the display screen. When a processing based on a characteristic indicator value while considering a sensor with low accuracy is performed, it becomes possible to perform preferable determination.

Moreover, the aforementioned identifying unit may calculate, for each time period, at least either of an area of a rectangle that is identified from each eye position and each accumulated movement amount within the time period and central coordinates of the rectangle to identify the transition of the movement directions of the eye gaze. Such a rectangle characterizes the trend of the eye gaze movement.

In addition, the aforementioned rectangle may be a rectangle that includes a second rectangle, which has an edge that is set according to the accumulated movement amount in each axis direction, and each eye position.

Furthermore, the aforementioned identifying unit may (a1) determine, for each time period, whether the accumulated movement amount of each eye position for the time period is within a predetermined range; (a2) when it is determined that the accumulated movement amount is within the predetermined range, calculate a reliability by dividing a number of eye gaze positions that was used for calculation of the accumulated movement amount by a number of eye gaze positions during the time period; and (a3) locate the second rectangle that has an edge whose length is obtained by multiplying the reliability by the accumulated movement amount that is within the predetermined range. Thus, while considering the reliability representing the effectiveness of the accumulated movement amount, the similarity can be calculated.

Incidentally, it is possible to create a program causing a computer or processor to execute the aforementioned processing, and such a program is stored in a computer readable storage medium or storage device such as a flexible disk, CD-ROM, DVD-ROM, magneto-optic disk, a semiconductor memory such as ROM (Read Only Memory), and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. An information processing apparatus, comprising:
a memory; and
a processor coupled to the memory and configured to execute:
identifying, for each of a plurality of users, transition of movement directions of an eye gaze of the user, from movement history of the eye gaze of the user on a display screen; and
extracting a minor user among the plurality of users based on the transition of the movement directions of the eye gaze, which is identified for each of the plurality of users, and
wherein the identifying comprises:
calculating, for each eye position and each axis direction, an accumulated movement amount from the eye position to an eye position for which transition of a direction is detected within a predetermined duration of time;
determining, for each time period and each axis direction, whether the accumulated movement amount calculated for each eye position in the time period is within a predetermined range;
calculating, for a time period and each axis direction, a reliability by dividing a number of first eye positions each of which is an eye position whose accumulated movement amount was determined to be within the predetermined range by a number of eye positions in the time period;
locating, for each first eye position in each time period, a first rectangle that has, in each axis direction, an edge whose length is obtained by multiplying the reliability, which is calculated for the axis direction and is calculated for the time period, by an accumulated movement amount which is calculated for the axis direction and is calculated for the first eye position in the time period; and calculating, for a time period, at least one of or any combination of an area of a second rectangle that includes eye positions and the first rectangle in the time period or central coordinates of the second rectangle to identify the transition of the movement directions of the eye gaze.

2. The information processing apparatus as set forth in claim 1, wherein the extracting of the minor user comprises:
comparing, for each time period, the transition of the movement directions of the eye gaze among the plurality of users to identify transition of movement directions of an eye gaze, which is presumed to be a majority of the plurality of users; and
extracting the minor user whose transition of the movement directions of the eye gaze is dissimilar to the identified transition of the movement directions of the eye gaze, which is presumed to be the majority of the plurality of users.

3. The information processing apparatus as set forth in claim 1, wherein the extracting the minor user comprises:
calculating, for each of the plurality of users, a similarity by comparing the transition of the movement directions of the eye gaze of the user with transition of movement directions of eye gazes of other users; and
determining, for each of the plurality of users and based on the similarity calculated for a user among the users, whether the user is the minor user.

4. A non-transitory computer-readable storage medium storing a program that causes a computer to execute a process, the process comprising:
identifying, for each of a plurality of users, transition of movement directions of an eye gaze of the user, from movement history of the eye gaze of the user on a display screen; and
extracting a minor user among the plurality of users based on the transition of the movement directions of the eye gaze, which is identified for each of the plurality of users, and
wherein the identifying comprises:
calculating, for each eye position and each axis direction, an accumulated movement amount from the eye position to an eye position for which transition of a direction is detected within a predetermined duration of time;
determining, for each time period and each axis direction, whether the accumulated movement amount calculated for each eye position in the time period is within a predetermined range;
calculating, for a time period and each axis direction, a reliability by dividing a number of first eye positions each of which is an eye position whose accumulated movement amount was determined to be within the predetermined range by a number of eye positions in the time period;
locating, for each first eye position in each time period, a first rectangle that has, in each axis direction, an edge whose length is obtained by multiplying the reliability, which is calculated for the axis direction and is calculated for the time period, by an accumulated movement amount which is calculated for the axis direction and is calculated for the first eye position in the time period; and
calculating, for a time period, at least one of or any combination of an area of a second rectangle that includes eye positions and the first rectangle in the time period or central coordinates of the second rectangle to identify the transition of the movement directions of the eye gaze.

5. An information processing method, comprising:
identifying, by using a computer and for each of a plurality of users, transition of movement directions of an eye gaze of the user, from movement history of the eye gaze of the user on a display screen; and
extracting, by using the computer, a minor user among the plurality of users based on the transition of the movement directions of the eye gaze, which is identified for each of the plurality of users, and
wherein the identifying comprises:
calculating, for each eye position and each axis direction, an accumulated movement amount from the eye position to an eye position for which transition of a direction is detected within a predetermined duration of time;
determining, for each time period and each axis direction, whether the accumulated movement amount calculated for each eye position in the time period is within a predetermined range;
calculating, for a time period and each axis direction, a reliability by dividing a number of first eye positions each of which is an eye position whose accumulated movement amount was determined to be within the predetermined range by a number of eye positions in the time period;
locating, for each first eye position in each time period, a first rectangle that has, in each axis direction, an edge whose length is obtained by multiplying the reliability, which is calculated for the axis direction and is calculated for the time period, by an accumulated movement amount which is calculated for the axis direction and is calculated for the first eye position in the time period; and
calculating, for a time period, at least one of or any combination of an area of a second rectangle that includes eye positions and the first rectangle in the time period or central coordinates of the second rectangle to identify the transition of the movement directions of the eye gaze.

\* \* \* \* \*